(12) United States Patent
Ling et al.

(10) Patent No.: US 10,060,847 B2
(45) Date of Patent: Aug. 28, 2018

(54) DETECTION AND SIGNAL PROCESSING SYSTEM FOR PARTICLE ASSAYS

(71) Applicant: Bio-Rad Laboratories, Inc., Hercules, CA (US)

(72) Inventors: Yunfeng Ling, Danville, CA (US); David P. Stumbo, Pleasanton, CA (US); George Carman, Livermore, CA (US); Denis Pristinski, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 56 days.

(21) Appl. No.: 15/394,624

(22) Filed: Dec. 29, 2016

(65) Prior Publication Data
US 2017/0191923 A1    Jul. 6, 2017

Related U.S. Application Data

(60) Provisional application No. 62/273,368, filed on Dec. 30, 2015.

(51) Int. Cl.
*G01N 15/14* (2006.01)

(52) U.S. Cl.
CPC ..... *G01N 15/1429* (2013.01); *G01N 15/1404* (2013.01); *G01N 15/1434* (2013.01); *G01N 2015/1488* (2013.01)

(58) Field of Classification Search
CPC ........... G01N 15/1404; G01N 15/1429; G01N 15/1434; G01N 2015/1488
(Continued)

(56) References Cited

U.S. PATENT DOCUMENTS

| 4,715,708 A | 12/1987 | Ito |
| 5,026,159 A * | 6/1991 | Allen ................. G01N 21/6428 |
| | | 250/458.1 |

(Continued)

FOREIGN PATENT DOCUMENTS

| WO | 2013189921 A1 | 12/2013 |
| WO | 2014186228 A1 | 11/2014 |
| WO | WO 2014186228 A1 * | 11/2014 ......... G01N 33/5094 |

OTHER PUBLICATIONS

Young, Lee W., Authorized Officer, International Searching Authority/US, Commissioner for Patents, "International Search Report" in connection with related International Application No. PCT/US2016/069334, 2 pages, dated Apr. 14, 2017.

(Continued)

*Primary Examiner* — David Porta
*Assistant Examiner* — Blake Riddick
(74) *Attorney, Agent, or Firm* — Kolisch Hartwell, P.C.

(57) ABSTRACT

Systems and methods for detecting and processing signals from particles. In an exemplary method, particles may be passed through a zone of a channel, while the zone is irradiated with light. Interaction of the light with the particles may deflect light and induce photoluminescence. A deflection signal and a photoluminescence signal may be detected from the zone. Particle waveforms may be identified in the deflection signal. At least a subset of the particle waveforms may be double-peak waveforms including a pair of peaks corresponding to a particle entering and exiting the zone. Amplitudes may be obtained from the photoluminescence signal. The amplitudes may correspond to respective particles and their particle waveforms, and at least a subset of the amplitudes may correspond to the double-peak waveforms. Individual particles may be assigned as positive or as (Continued)

negative for an analyte based on the corresponding amplitudes.

21 Claims, 18 Drawing Sheets

(58) Field of Classification Search
USPC .............................. 250/458.1, 459.1, 461.2
See application file for complete search history.

(56) References Cited

U.S. PATENT DOCUMENTS

| | | | |
|---|---|---|---|
| 5,190,857 A * | 3/1993 | Allen ................ | G01N 21/6428 250/459.1 |
| 5,684,584 A | 11/1997 | Nakamoto et al. | |
| 5,872,627 A | 2/1999 | Miers | |
| 6,023,324 A | 2/2000 | Myers | |
| 6,166,804 A * | 12/2000 | Potyrailo ............ | G01N 21/643 250/458.1 |
| 6,180,415 B1 | 1/2001 | Schultz et al. | |
| 6,193,850 B1 * | 2/2001 | Potyrailo ............ | G01N 21/64 204/157.15 |
| 6,254,831 B1 * | 7/2001 | Barnard ............. | G01N 21/6428 250/458.1 |
| 6,437,345 B1 * | 8/2002 | Bruno-Raimondi . | G01N 21/474 250/252.1 |
| 6,640,197 B2 * | 10/2003 | Pittaro ................ | G01N 21/253 250/458.1 |
| 7,433,552 B2 * | 10/2008 | Kiesel ................ | G01J 1/42 250/339.12 |
| 7,714,301 B2 * | 5/2010 | Jackson ............. | G01N 21/6456 250/458.1 |
| 2002/0109100 A1 | 8/2002 | Jackson, III ....... | G01N 21/6456 250/458.1 |
| 2002/0158212 A1 * | 10/2002 | French ............... | B01L 3/50853 250/459.1 |
| 2003/0127609 A1 * | 7/2003 | El-Hage ............. | G01N 21/253 250/574 |
| 2006/0237665 A1 * | 10/2006 | Barney .............. | G01N 15/1459 250/458.1 |
| 2007/0281288 A1 * | 12/2007 | Belkin .............. | B01L 3/502715 435/4 |
| 2008/0138848 A1 * | 6/2008 | Li ..................... | B01L 3/502761 435/29 |
| 2008/0241843 A1 * | 10/2008 | Zare .................. | G01J 3/02 435/6.12 |
| 2008/0246946 A1 | 10/2008 | Hansen et al. | |
| 2008/0272313 A1 * | 11/2008 | Van Herpen ....... | G01N 21/6428 250/459.1 |
| 2008/0302976 A1 * | 12/2008 | Van Herpen ....... | G01N 21/6456 250/459.1 |
| 2009/0008573 A1 * | 1/2009 | Conner .............. | H01L 33/507 250/459.1 |
| 2009/0224173 A1 * | 9/2009 | Duveneck .......... | G01N 21/6428 250/459.1 |
| 2009/0250630 A1 * | 10/2009 | Van Der Zaag ... | G01N 21/6428 250/459.1 |
| 2009/0309049 A1 * | 12/2009 | Van Dijk ........... | G01J 3/02 250/578.1 |
| 2010/0173394 A1 | 7/2010 | Colston, Jr. et al. | |
| 2011/0044858 A1 * | 2/2011 | Jaffe ................. | G01J 3/10 422/82.08 |
| 2011/0101243 A1 * | 5/2011 | Wimberger-Friedl ............ | G01N 21/6452 250/459.1 |
| 2011/0222062 A1 * | 9/2011 | Martini .............. | G01N 21/05 356/417 |
| 2012/0104280 A1 * | 5/2012 | Manian ............. | G01N 21/6428 250/459.1 |
| 2012/0194805 A1 | 8/2012 | Ness et al. | |
| 2012/0252015 A1 * | 10/2012 | Hindson ............ | C12Q 1/6883 435/6.11 |
| 2013/0092846 A1 * | 4/2013 | Henning ........... | G01N 21/6408 250/458.1 |
| 2014/0030696 A1 * | 1/2014 | Luscher ............ | G01N 15/1404 435/3 |
| 2014/0221239 A1 | 8/2014 | Carman et al. | |
| 2014/0370586 A1 | 12/2014 | Seo et al. | |
| 2015/0144806 A1 * | 5/2015 | Jin ................... | G01N 21/6408 250/461.2 |
| 2016/0003732 A1 * | 1/2016 | Li ..................... | G01N 21/648 356/301 |

OTHER PUBLICATIONS

Young, Lee W., Authorized Officer, International Searching Authority/US, Commissioner for Patents, "Written Opinion of the International Searching Authority" in connection with related International Application No. PCT/US2016/069334, 5 pages, dated Apr. 14, 2017.

* cited by examiner

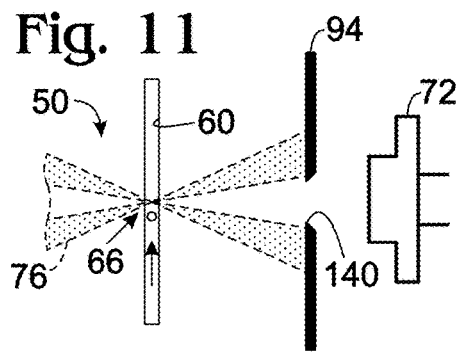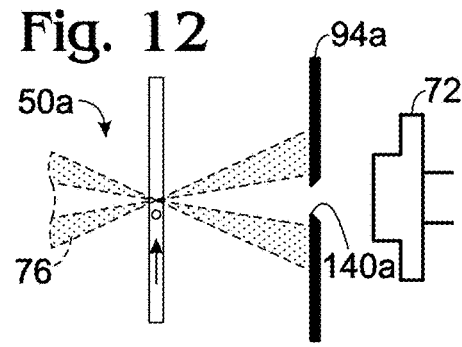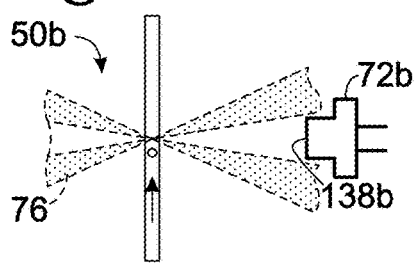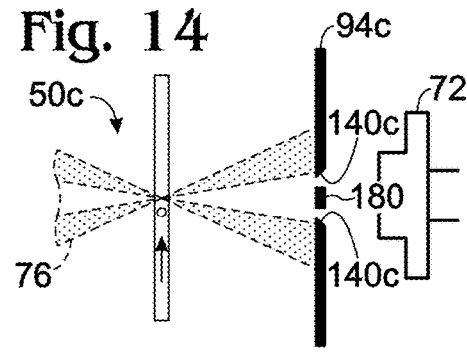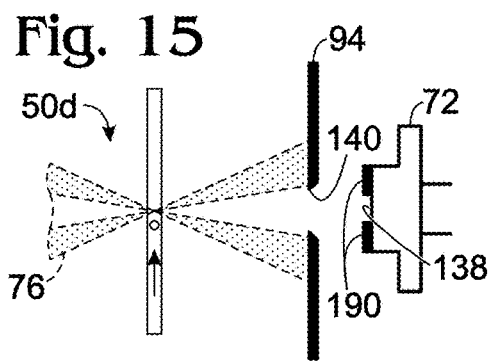

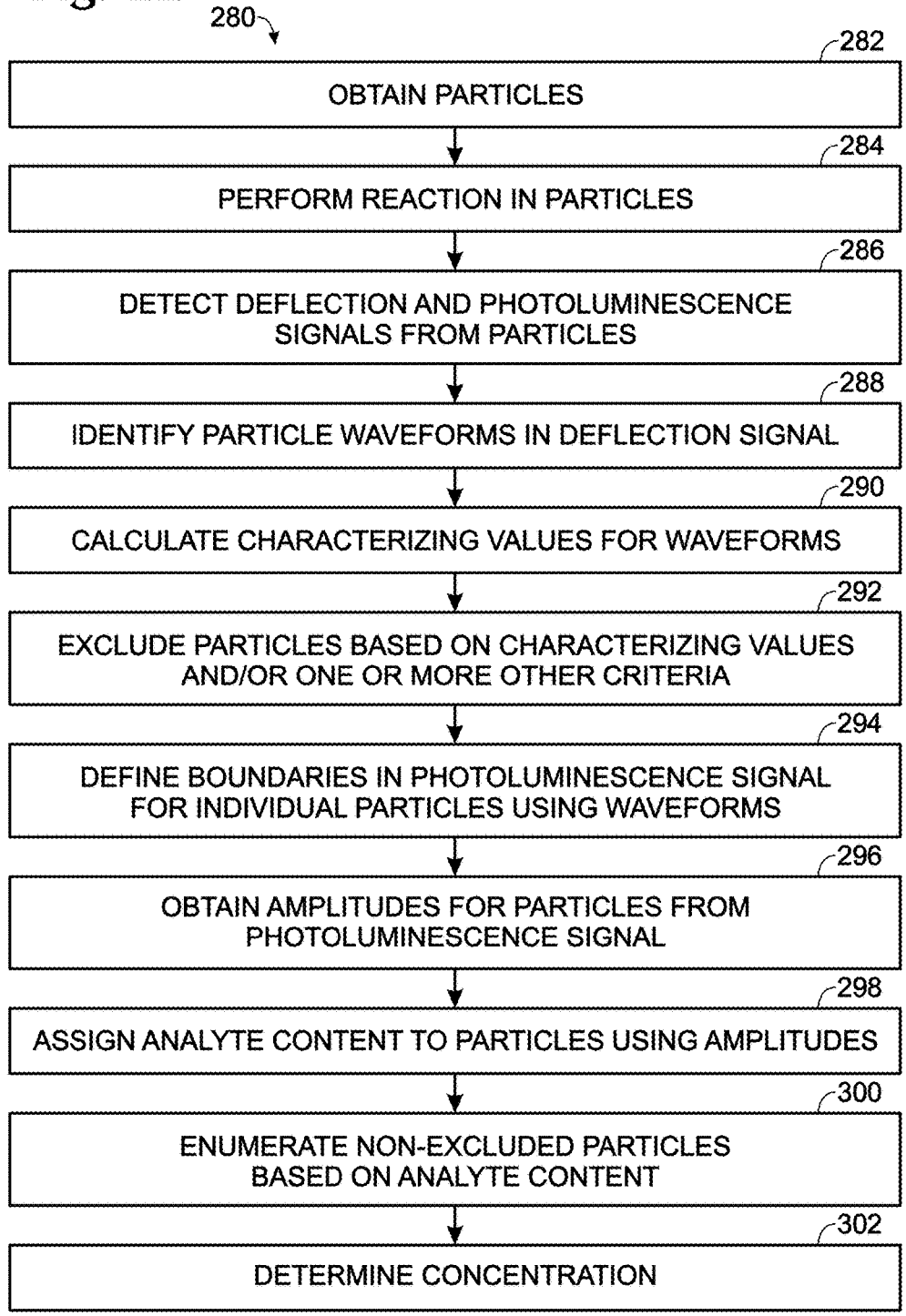

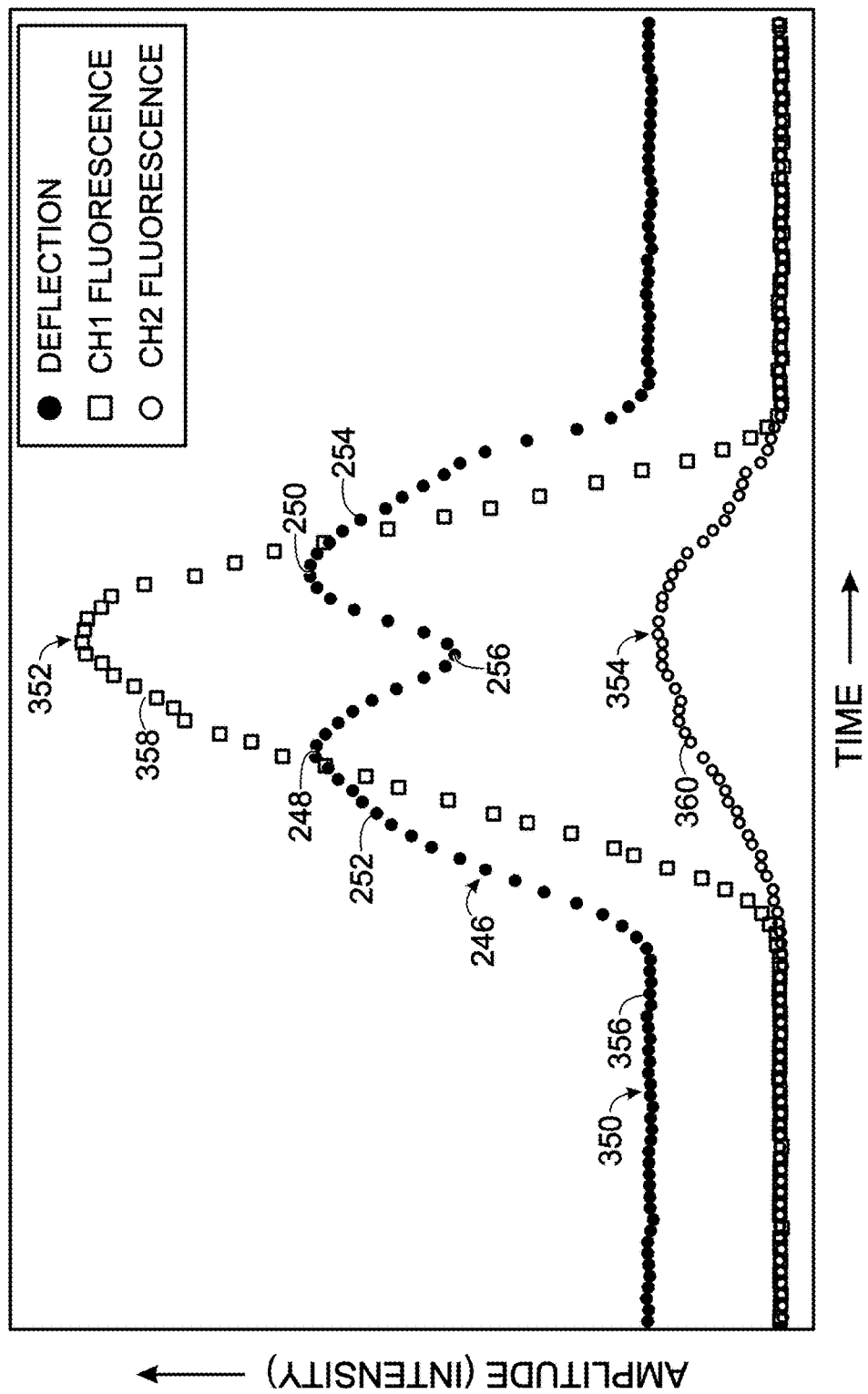

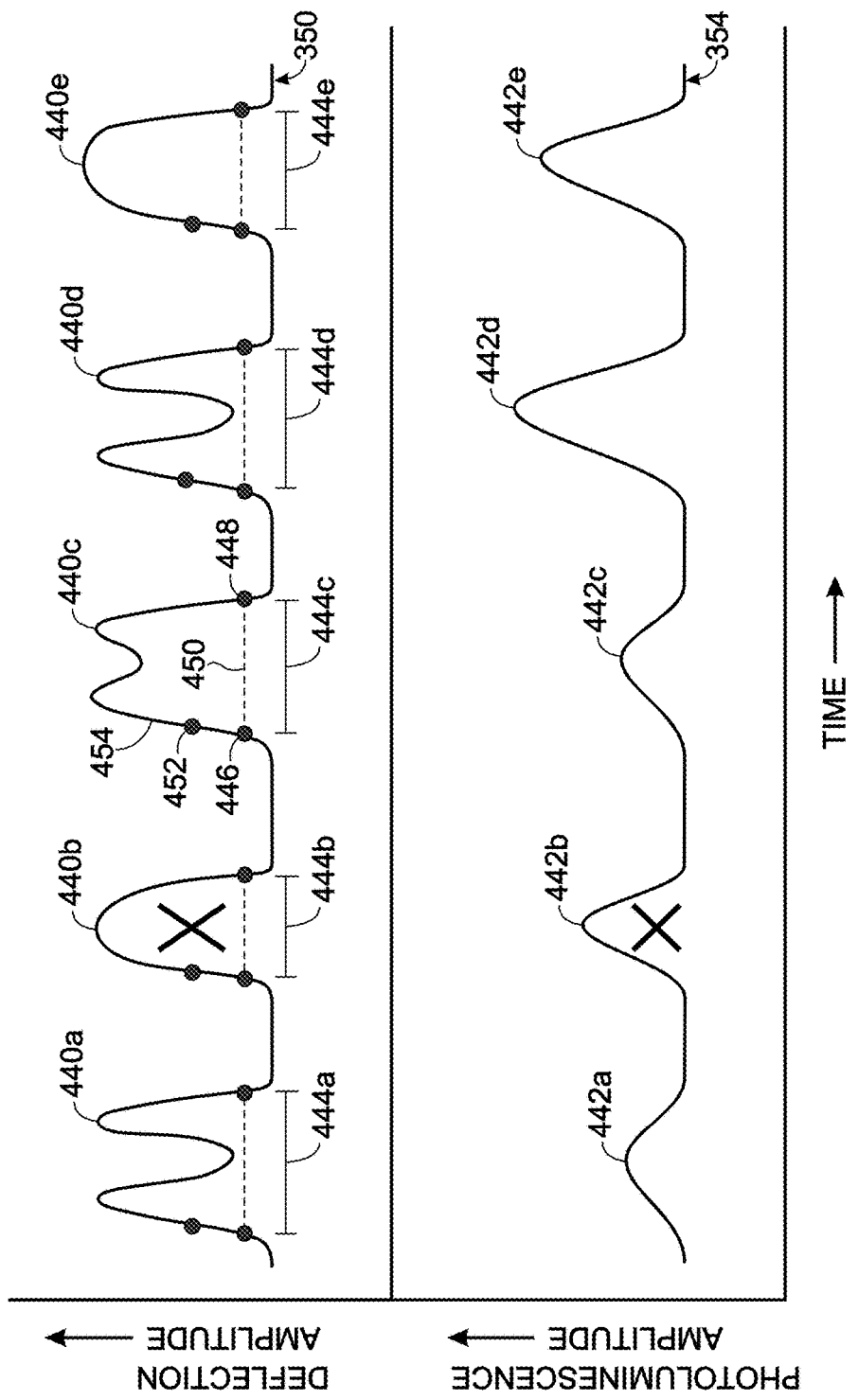

DETECTION AND SIGNAL PROCESSING SYSTEM FOR PARTICLE ASSAYS

CROSS-REFERENCE TO PRIORITY APPLICATION

This application is based upon and claims the benefit under 35 U.S.C. § 119(e) of U.S. Provisional Patent Application Ser. No. 62/273,368, filed Dec. 30, 2015, which is incorporated herein by reference in its entirety for all purposes.

CROSS-REFERENCES TO OTHER MATERIALS

This application incorporates by reference in their entirety for all purposes the following: U.S. Patent Application Publication No. 2010/0173394 A1, published Jul. 8, 2010; and Joseph R. Lakowicz, PRINCIPLES OF FLUORESCENCE SPECTROSCOPY (2nd Ed. 1999).

INTRODUCTION

A signal is detected from particles, such as droplets, in various types of assays. In a typical assay, the particles are labeled with a fluorescent dye. Fluorescence then is detected from individual particles as the particles are passed serially through a detection volume where the fluorescent dye is excited to cause light emission.

Fluorescence alone may be inadequate to accurately detect the presence of each particle and characterize the particle's size/shape. This problem can be significant in a mixed population of particles each having high or low fluorescence, as in many digital assays. Accordingly, the results of a particle-based assay may be skewed by overestimating or underestimating the number of particles detected, failing to exclude fluorescence data for particles that do not meet predefined criteria, or the like.

SUMMARY

The present disclosure provides systems and methods for detecting and processing signals from particles. In an exemplary method, particles may be passed through a zone of a channel, while the zone is irradiated with light. Interaction of the light with the particles may deflect light and induce a photoluminescence. A deflection signal and a photoluminescence signal may be detected from the zone. Particle waveforms may be identified in the deflection signal. At least a subset of the particle waveforms may be double-peak waveforms including a pair of peaks corresponding to a particle entering and exiting the zone. Amplitudes may be obtained from the photoluminescence signal. The amplitudes may correspond to respective particles and their particle waveforms, and at least a subset of the amplitudes may correspond to the double-peak waveforms. Individual particles may be assigned as positive or as negative for an analyte based on the corresponding amplitudes.

BRIEF DESCRIPTION OF THE DRAWINGS

FIG. 11 is a fragmentary view of the detection and processing system of FIG. 1 taken around a flow channel and a deflection detector of the system.

FIG. 12 is a fragmentary view of a modified version of the detection and processing system of FIG. 1, taken as in FIG. 11 and having a narrower optical slit between the flow channel and the deflection detector, to reduce detection of small angle deflection.

FIG. 13 is a fragmentary view of another modified version of the detection and processing system of FIG. 1, taken as in FIG. 11 and having a deflection detector with a smaller photosensitive area located in the image plane of the mask and replacing the optical slit of FIG. 11.

FIG. 14 is a fragmentary view of still another modified version of the detection and processing system of FIG. 1, taken as in FIG. 11 and having a pair of optical slits located in the image plane of the mask to reduce detection of large angle deflection.

FIG. 15 is a fragmentary view of yet another modified version of the detection and processing system of FIG. 1, taken as in FIG. 11 and having a portion of the deflection detector masked to reduce detection of undesired light.

FIG. 16 is a fragmentary view of an embodiment of the detection and processing system of FIG. 1 configured to detect deflected light and undeflected light at a position downstream of the irradiation zone of the channel.

FIG. 17 is a calculated intensity distribution of light within the detection and processing system of FIG. 16 for a region indicated generally by line 17-17 in FIG. 16 and located in and around the irradiation zone.

FIG. 18 is a calculated intensity distribution of light incident on a detector of the system of FIG. 16 at the region indicated generally by line 18-18 in FIG. 16.

FIG. 22 is a flowchart of exemplary steps that may be performed in a method of particle analysis for at least one analyte, in accordance with aspects of the present disclosure.

FIG. 24 is a graph of the deflection and fluorescence signals detected with a working model of the detection and processing system of FIG. 19 before, during, and after passage of a single droplet through the detection volume of a channel.

FIG. 31 is a pair of graphs schematically depicting a deflection signal and a photoluminescence signal detected over the same time period from droplets (or other particles) passing serially through an irradiation zone of a channel, with the graphs schematically illustrating a filtering process that may be performed to exclude droplets (or other particles) corresponding to single-peak or double-peak waveforms having width values outside an acceptable range, in accordance with aspects of the present disclosure.

DETAILED DESCRIPTION

Figure 1:
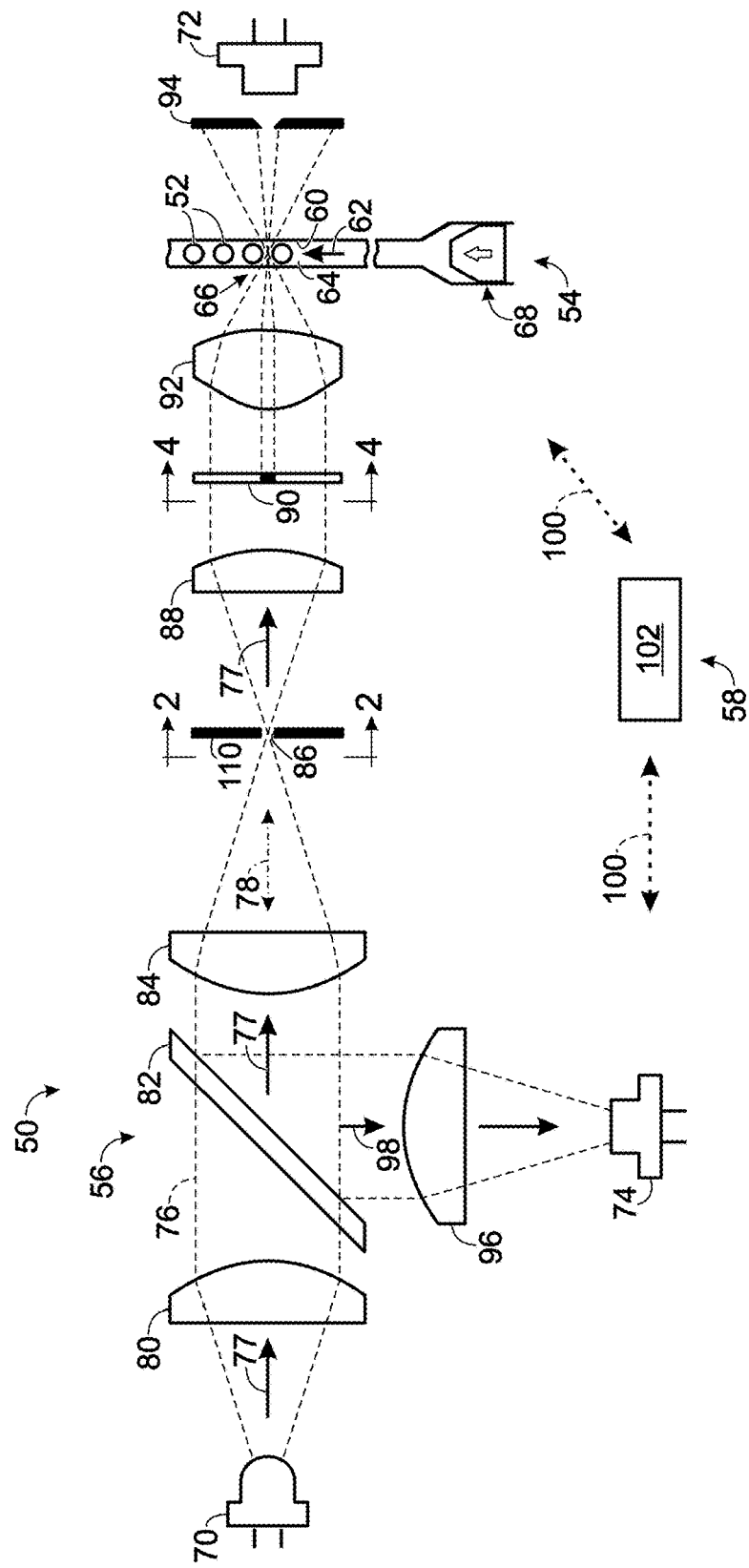
FIG. 1 is a schematic view of an exemplary system for detecting and processing signals from particles, such as droplets, in accordance with aspects of the present disclosure.

The present disclosure provides systems and methods for detecting and processing signals from particles. In an exemplary method, particles may be passed through a zone of a channel, while the zone is irradiated with light. Interaction of the light with the particles may deflect light and induce photoluminescence. A deflection signal and a photoluminescence signal may be detected from the zone. Particle waveforms may be identified in the deflection signal. At least a subset of the particle waveforms may be double-peak waveforms including a pair of peaks corresponding to a particle entering and exiting the zone. Amplitudes may be obtained from the photoluminescence signal. The amplitudes may correspond to respective particles and their particle waveforms, and at least a subset of the amplitudes may correspond to the double-peak waveforms. Individual particles may be assigned as positive or as negative for an analyte based on the corresponding amplitudes.

In some embodiments, the method further may include any combination of the following. A width value may be calculated for each waveform, and particles may be excluded based on the width values. In some embodiments, the width value may be a separation value corresponding to a time interval between a pair of peaks of the waveform. In some embodiments, each width value may be compared to a threshold, and a corresponding particle (and corresponding amplitude(s) and waveform) may be excluded if the comparison meets a predefined condition. The step of obtaining amplitudes may include a step of calculating an integrated amplitude based on integration boundaries defined with a corresponding waveform and, optionally, defined using a pair of time points at which a width value of the waveform is calculated.

An exemplary system for detecting and processing signals from particles is provided. The system may comprise a channel and one or more light sources configured to irradiate a zone within the channel. The system also may comprise at least one source of positive/negative pressure configured to drive particles in a carrier fluid through the zone. The system further may comprise a deflection detector configured to detect a deflection signal from particles passing through the zone, and a photoluminescence detector configured to detect a photoluminescence signal from particles passing through the zone. The system still further may comprise a processor. The processor may be configured to identify particle waveforms in the deflection signal. At least a subset of the particle waveforms may be double-peak waveforms including a pair of peaks corresponding to a particle entering and exiting the zone. The processor also may be configured to obtain amplitudes from the photoluminescence signal. The amplitudes may correspond to respective particles and their particle waveforms. At least a subset of the amplitudes may correspond to the double-peak waveforms. The processor further may be configured to assign individual particles as positive or as negative for an analyte based on the corresponding amplitudes.

In some embodiments, the processor may be configured further as follows. The processor may be configured to calculate a width value for each waveform of a plurality of the waveforms, and to exclude particles (and corresponding amplitudes and/or waveforms) based on the width values. Each width value may be a separation value corresponding to a time interval between the pair of peaks of a waveform. The processor also or alternatively may be configured to adjust the width values calculated from the waveforms to correct for fluctuations in flow rate of a fluid carrying particles through the zone as the signals are being detected, and to exclude particles (and corresponding signal portions) based on adjusted width values. In some embodiments, the processor may be configured to adjust the width values with a spline. For example, the processor may replace the width values with a spline fit and use the residuals of the fit to adjust width values. Also or alternatively, the processor may be configured to calculate an average of the width values, and to exclude particles temporally corresponding to width values that deviate by more than a defined amount from the average. Also or alternatively, the processor may be configured to compare each width value to a threshold (or range), and to exclude particles temporally corresponding to width values that exceed (or are less than) the predefined threshold (or are outside the predefined range). In some embodiments, the processor may be configured to identify double-peak waveforms and/or single-peak waveforms with a state machine, optionally in real time. Each amplitude may be an integrated amplitude, and the processor also or alternatively may be configured to obtain integrated amplitudes from portions of the photoluminescence signal based on integration boundaries defined with each waveform, and the number of particles assigned as positive or negative for the analyte may be determined based on integrated amplitudes. The integration boundaries optionally may be defined using time points at which the corresponding width value is calculated.

The systems and methods of the present disclosure may offer various advantages for particle assays, including either or both of the following.

First, size information about each particle may be determined from a deflection signal instead of a photoluminescence signal (e.g., a fluorescence signal). Photoluminescence signal amplitude may vary dramatically among particles according to the analyte content of each particle. Each particle positive for an analyte being tested generally produces a higher signal amplitude, resulting in a greater estimated size of the positive particle, while each particle negative for the analyte produces a lower signal amplitude, resulting in a lesser estimated size of the negative particle. In contrast, the amplitude of the deflection signal is the same for both positive and negative particles. Accordingly, the deflection signal may be used to filter particles according to size, with little or no bias produced by analyte content, which results in more accurate analyte measurements.

Second, integrated amplitude information may be obtained for each particle by integrating a portion of the photoluminescence signal. This integration approach may produce integrated amplitudes that are proportional to the effective number of dye molecules in each particle (e.g., the number of unquenched and/or bound dye molecules). Accordingly, these integrated amplitudes may be affected less by geometry and/or size changes of the particles caused, for example, by deformation, shrinkage, etc., resulting in further improvement in the accuracy of analyte measurements.

Further aspects of the present disclosure are described in the following sections: (I) detection and signal processing system overview, (II) fluidics subsystem, (III) optical subsystem, (IV) methods of particle detection, (V) detection configurations for deflected light, (VI) exemplary intensity distributions of deflected light, (VII) detection and processing system embodiment, (VIII) exemplary deflection and photoluminescence signals, (IX) overview of assays with particles, (X) exemplary algorithms for signal processing, and (XI) examples.

I. DETECTION AND SIGNAL PROCESSING SYSTEM OVERVIEW

This section provides an overview of an exemplary detection and signal processing system 50 for optically detecting and/or characterizing particles 52, such as droplets; see FIGS. 1-8. Detection and processing system 50 may include a fluidics subsystem 54, an optical subsystem 56, and a processing/control subsystem 58. In some embodiments, the system may be described as a detection system.

Fluidics subsystem 54 may incorporate a channel 60 at which the fluidics subsystem intersects the optical subsystem. The channel defines a flow path for travel, indicated by a motion arrow at 62, of particles 52 and a surrounding carrier fluid 64. The flow path extends through an irradiation zone 66 within the channel. (The irradiation zone 66 interchangeably may be called a detection volume, as explained below.) The fluidics subsystem also includes a drive mechanism operatively connected to the channel and including one or more sources of positive/negative pressure. Each source of positive/negative pressure may, for example, include at least one pump 68 that is operatively connected to the channel, to create a pressure differential that drives flow of the carrier fluid along channel 60 and through irradiation zone 66. The pump may be a positive pressure pump or a negative pressure pump (i.e., a vacuum pump). Fluid communication between the pump and the channel may be controlled by one or more valves located in a fluid path between the pump and the channel.

Particles 52 are transported by the carrier fluid through the irradiation zone. The carrier fluid may be supplied by a source of carrier fluid that is in fluid communication with the channel. In some embodiments, the particles may be droplets, such as aqueous droplets, and the carrier fluid may be a continuous phase, such as oil, composed of liquid that is immiscible with the droplets.

Optical subsystem 56 includes at least one light source 70, at least one light detector (e.g., a deflection detector 72 and a photoluminescence detector 74), and various optical elements to direct and/or restrict travel of optical radiation from the light source(s) to irradiation zone 66, and from the irradiation zone to the detector(s). Light source 70 may generate a beam 76 of optical radiation, which may, for example, be diverging, collimated, or converging in regions along the beam, according to the optical elements disposed in the path of the beam. The optical subsystem may incorporate any suitable optical elements, such as lenses, masks, spatial/spectral filters, mirrors, aperture-defining elements, beam splitters, light guides, and the like. For example, one or more spectral filters may be disposed in an optical path between the irradiation zone and the photoluminescence detector to selectively prevent excitation light (relative to light emitted by photoluminescence) from reaching the detector.

The terms "light" and "optical radiation" are used interchangeably in the present disclosure. Either term denotes ultraviolet radiation, visible light, or infrared radiation, or any combination thereof.

Beam 76 follows on an optical path 77 extending downstream from light source 70, across channel 60, and toward deflection detector 72. The optical path defines an optical axis 78 that may be linear, as shown here, or may be bent (e.g., via a light guide and/or a mirror) (see Example 3). In the depicted embodiment, following the beam from light source 70 along optical path 77, beam 76 diverges, is collimated by a collimating lens 80, extends through a beam splitter 82 (here, a short-pass mirror), and is focused by a focusing lens 84. The focused beam extends through an optical slit 86, is collimated by another collimating lens 88, and partially blocked by mask 90. The beam is focused by at least one focusing element on irradiation zone 66 of channel 60. The focusing element(s) may be described as a condenser and as an objective. The focusing element(s) functions as a condenser for optical radiation of beam 76 traveling from left to right in FIG. 1 along optical path 77, and as an objective for emitted light traveling in reverse, from right to left in FIG. 1, along only a portion of the optical path. The focusing element(s) is called objective 92.

At any given time, optical radiation incident on irradiation zone 66 may follow different trajectories. Most of the optical radiation of the beam may pass through irradiation zone 66 substantially undeflected. This undeflected optical radiation is not incident on the photosensitive region of deflection detector 72. For example, this undeflected optical radiation may be prevented from reaching detector 72 by a spatial filter, namely, an aperture-defining element (e.g., a slit-forming element 94), or may be too divergent from the optical path to detector 72. A fraction of the optical radiation may be deflected sufficiently toward the deflection detector by the current contents of the irradiation zone, such that the deflected radiation is incident on a photosensitive area of the detector and thus is detected. Another fraction of the optical radiation may excite a photoluminophore(s) within the irradiation zone, causing emission of photons (i.e., photoluminescence).

A portion of this emitted light may be detected by photoluminescence detector 74, after travel in reverse along a portion of optical path 77. In particular, the emitted light passes through objective 92, collimating (now focusing) lens 88, optical slit 86, and focusing (now collimating) lens 84. When the emitted light (of longer wavelength than the excitation light of beam 76) reaches beam splitter 82, the light is reflected to a focusing lens 96, indicated by an arrow at 98, which focuses the emitted light on photoluminescence detector 74. Accordingly, optical radiation from the same light source 70 may be deflected toward deflection detector 72 and may cause photoluminescence.

The term "deflect," as used herein, means cause to change course or follow a new trajectory. More specifically, optical radiation deflected by interaction with matter (e.g., a particle and/or carrier fluid) in an irradiation zone deviates from a current trajectory as a consequence of the interaction. Deflection may occur by any suitable mechanism or combination of mechanisms. Exemplary deflection mechanisms pertinent to the detection system disclosed herein may include refraction, reflection, Mie scattering, and the like. In some embodiments, such as with transparent particles, a difference in refractive index between the particles and the carrier fluid may be responsible for a majority of the detected deflection. "Deflection" interchangeably may be described as "scattering," "deflect" as "scatter," and "deflected" as "scattered."

To facilitate description, light can be considered to travel in the beam along an optical path from positions optically "upstream" to positions optically "downstream." Accordingly, the relative position of optical elements in the optical path also can be described with these two terms. For example, in FIG. 1, light source 70 is upstream of optical slit 86, which, in turn, is upstream of mask 90. The mask is upstream of objective 92 and irradiation zone 66. Deflection detector 72 and slit-forming element 94 are downstream of irradiation zone 66, and slit-forming element 94 is upstream of detector 72.

Processing/control subsystem 58 may be in communication with and/or operatively connected to any suitable components of the fluidics subsystem and/or the optical subsystem, as indicated by arrows 100. For example, subsystem 58 may receive a deflection signal detected by deflection detector 72 and/or a photoluminescence signal detected by photoluminescence detector 74. Subsystem 58 may include a processor 102 (e.g., an electronic/digital processor) configured to process the deflection signal and/or the photoluminescence signal to determine one or more characteristics of particles 52. The characteristics may include a size, velocity, shape, transit time through the irradiation zone, presence or absence of an analyte in or on individual particles, or the like. Processor 102 also or alternatively may control operation of pump 68, light source 70, or one or both detectors 72 and 74, or any combination thereof.

Processor 102 may include a memory and a data manipulation program stored in the memory. The data manipulation program may include instructions stored in memory and executable by the processor to control and/or perform any of the steps of the present disclosure.

Figure 2:
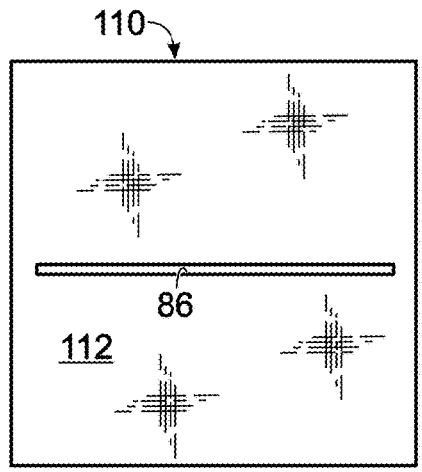
FIG. 2 is a view of a slit-forming optical element of the detection and processing system of FIG. 1, taken generally along line 2-2 of FIG. 1.

FIG. 2 shows a slit-forming optical element 110 of detection and processing system 50 that creates optical slit 86. The slit is transparent for the optical radiation of the system, while an opaque body 112 around the slit prevents transmission of the optical radiation through optical element 110 elsewhere. Slit 86 may, for example, be created by an opening (an air gap) in body 112 or as an unmasked area on an otherwise masked surface of body 112. The slit is elongated orthogonal to optical path 77 followed by beam 76 at optical element 110, and elongated orthogonal to a direction of elongation of channel 60 (and fluid flow) through irradiation zone 66 (after correcting for a change in direction, if any, in the optical path between optical slit 86 and irradiation zone 66 (e.g., a change in direction created by a mirror)).

Figure 3:
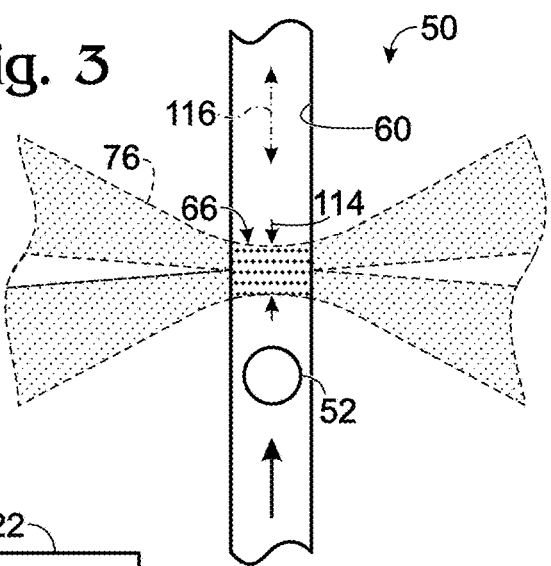
FIG. 3 is a fragmentary view of the detection and processing system of FIG. 1, taken where a light beam intersects a flow channel to create an irradiation zone, also called a detection volume.

FIG. 3 shows irradiation zone 66 of channel 60 in more detail. Optical elements located in the optical path between slit 86 and channel 60 may collimate beam 76 and then focus the beam 76 on a section of the channel. The channel may be elongated in an image plane of slit 86 (see FIG. 1), such that the slit is projected onto the section of the channel to create a volume within the channel that is irradiated by beam 76. This volume, which is stippled distinctly in FIG. 3, is equivalent to irradiation zone 66, and may be described as a detection volume because the changing contents of this volume, as carrier fluid and particles flow through channel 60, may be a primary determinant of how much light is sensed by each detector over time.

The width of slit 86 and the magnification or minification, if any, created by optical elements between the slit and irradiation zone 66, define a projected width 114 of the slit in channel 60. Projected slit width 114, measured parallel to a local long axis 116 of the channel, determines the size of irradiation zone 66 within the channel. For example, if slit 86 has a width of 35 µm, and the optical subsystem has a magnification of two between slit 86 and channel 60, projected width 114 is 70 µm. Accordingly, the width of slit 86 may, for example, be selected according to the diameter (or length) of particles 52 being detected, such that projected slit width 114 is less than a dimension of particles 52 (e.g., the diameter (or length) thereof). In exemplary embodiments, the projected slit width is about 40-90%, 50-80%, or 60-70% of the particle dimension. The dimension of the particles is defined in channel 60, and is measured parallel to the direction of particle travel, as each particle passes through the irradiation zone. The dimension (e.g., length) of each particle may be substantially the same as its diameter or may be substantially greater than the diameter, such as at least 20%, 30%, 40%, or 50% greater than the diameter, among others.

Figure 4:
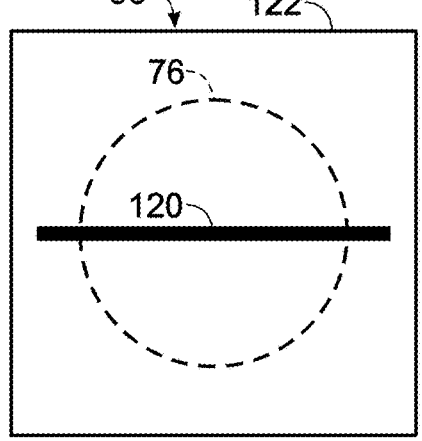
FIG. 4 is a view of a mask of the detection and processing system of FIG. 1, taken generally along line 4-4 of FIG. 1.

FIG. 4 shows mask 90 of detection and processing system 50. The mask may block any suitable transverse portion of the beam. For example, the mask may be a line mask that provides a narrow, elongated, non-transmissive region, namely, a line 120 to block a portion of beam 76. Line 120 may be oriented parallel to optical slit 86, and may or may not be centered on beam 76 and/or optical axis 78. The mask may, for example, be formed by a transparent substrate 122 having an opaque coating to create an opaque line 120. For example, substrate 122 may be formed of glass, and line 120 may be produced by chromium etching of an elongated surface region of the glass. The mask may be considered to be the entire optical element or only an opaque region thereof. In some examples, the line mask may be created by a discrete elongated member, such as a thin wire. In some examples, the mask may have a different shape of masking element, such as a non-elongated shape (e.g., a circle or square) to create a point mask.

Line 120 may have any suitable size and position. The line may be longer than the diameter of beam 76, as shown in FIG. 4. The width of line 120 may be substantially less than the beam's diameter, such as less than about 20%, 10%, or 5%, among others, of the diameter. The line may block any suitable portion of the beam's cross-sectional area (and/or light), such as less than about 10%, 5%, or 2%, among others. Exemplary widths of line 120 include less than about 1 mm, 700 μm, or 400 μm, among others.

Figure 5:
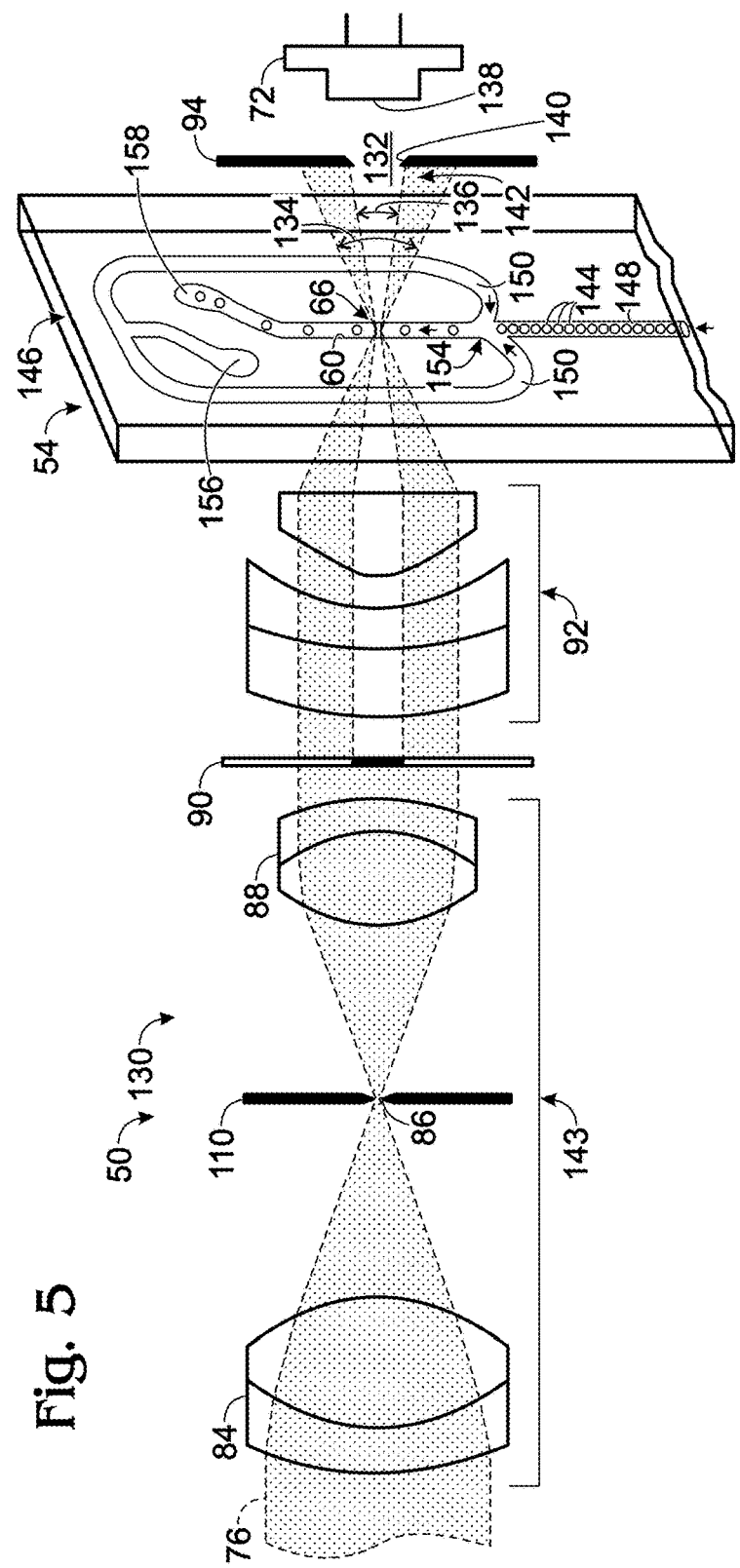
FIG. 5 is a fragmentary, schematic view of an embodiment of the detection and processing system of FIG. 1, with the beam of light stippled to illustrate how a mask forms a shadow region in the beam, in accordance with aspects of the present disclosure.

FIG. 5 shows an embodiment 130 of detection and processing system 50. Beam 76 is stippled to illustrate how mask 90 blocks a portion of the beam to form a shadow region 132 (interchangeably termed a dark region) in the beam. Portions of the shadow region may be located optically upstream and downstream of the irradiation zone (and channel 60). However, in the depicted embodiment, the downstream portion provides a location for detection of deflected light. The shadow region may represent any suitable portion of a beam angle 134 defined by a diverging region of the beam extending away from channel 60 toward deflection detector 72. For example, the shadow region may define a shadow region angle 136 of less than about 8, 6, 5, 4, 3, or 2 degrees, among others.

Deflection detector 72 has a photosensitive area 138 that is aligned with shadow region 132. An optical slit 140 defined by optical element 94 is sized and positioned to prevent undeflected light 142 of beam 76 from striking photosensitive area 138. In other words, optical slit 140 may be narrower than the width of shadow region 132 where the beam strikes optical element 94. Optical slit 140 may be located in the image plane of mask 90. Deflection detector 72 is positioned behind (downstream from) optical element 94 and its slit 140 and detects light from beam 76 that is deflected into the shadow region.

A suitable position for slit 140 and/or deflection detector 72 may be determined by the proximity of mask 90 to the back focal plane of objective 92. If the mask is placed in this focal plane, the image plane for the mask is located at infinity behind channel 60. Accordingly, the mask can be positioned with an offset from the back focal plane to move the mask's image plane to a convenient distance from channel 60. Photosensitive area 138 of detector 72 may be positioned near the image plane of the mask, such as close to and directly behind slit 140. Alternatively, or in addition, light that has passed through the irradiation zone, and particularly deflected light, can be focused with an optical element, as described below in Example 1.

In order to achieve a high signal-to-noise ratio, the slit may be located in the mask's image plane. Moving the slit closer to or farther from the objective, and therefore out of the image plane, rapidly reduces contrast of the mask image and increases noise. The contrast is reduced because the slit has a finite width, and the light coming though it may not be perfectly collimated when incident on the mask. An idealized, masked beam pattern (i.e., a sharp mask shadow at any downstream position), shown in FIG. 1, only may occur for a mask inserted in a perfectly collimated beam.

A mask image formed in an image plane of mask may or may not be magnified or minified with respect to the physical mask. In the depicted embodiment, the image of the mask is minified 0.5× relative to the physical mask. For example, if a line of the physical mask has a width of 300 μm, the width of the line in the mask image may be 150 μm.

Detection and processing system 130 illustrates additional exemplary aspects of system 50 of FIG. 1. For example, system 130 incorporates an objective 92 formed by two or more lenses, which may be pre-assembled with one another to create a unit. In the depicted embodiment, the objective is a Meiji objective having 40× magnification, a numerical aperture of 0.6, and a working distance of 2.8 mm. A spatial filter 143 providing a 2× magnification is formed by lenses 84 and 88, and slit-forming optical element 110. Also, fluidics subsystem 54 is designed to transport droplets 144 (as particles 52) through irradiation zone 66 in a channel-forming member 146 that is planar. The droplets are disposed in an immiscible carrier liquid 148 (e.g., oil). The separation, if any, between droplets approaching irradiation zone 66 may be increased by introduction of additional carrier fluid 150 from one or more dilution channels at a channel junction 154 that is fluidically upstream of irradiation zone 66. Channel member 146 also may have an inlet 156 for ingress of additional carrier fluid and an outlet 158 for egress of droplets 144 after passing through the irradiation zone.

Figure 6:
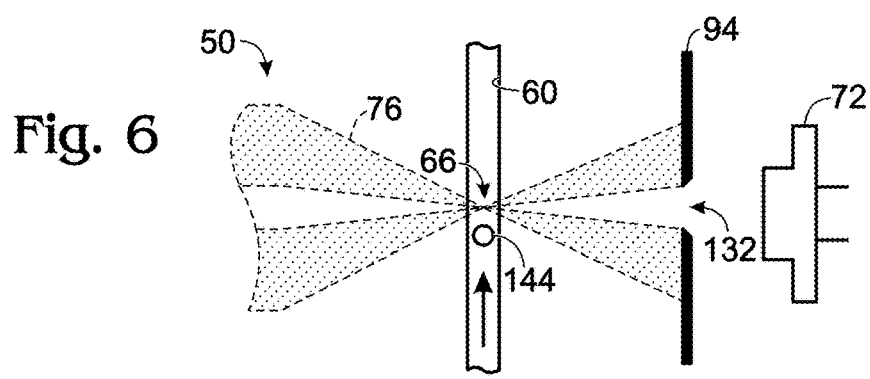
FIGS. 6-9 are a temporal series of fragmentary views of the detection and processing system of FIG. 1, taken as a particle (e.g., a droplet) passes through the detection volume of the system and illustrating how incident light may be deflected by different regions of the particle, in accordance with aspects of the present disclosure.
Figure 7:
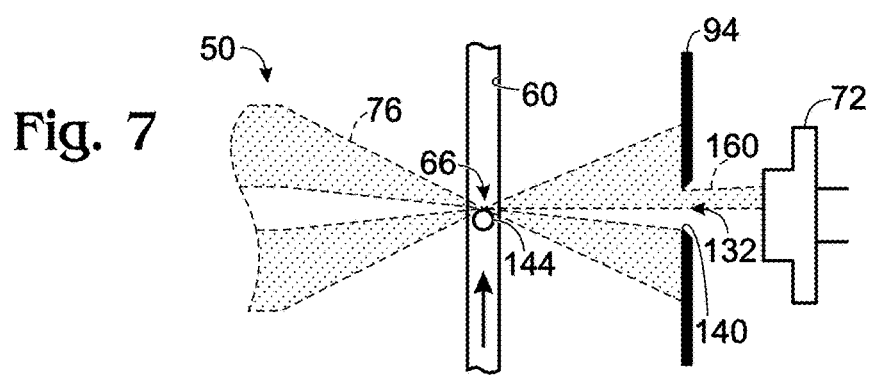
Figure 8:
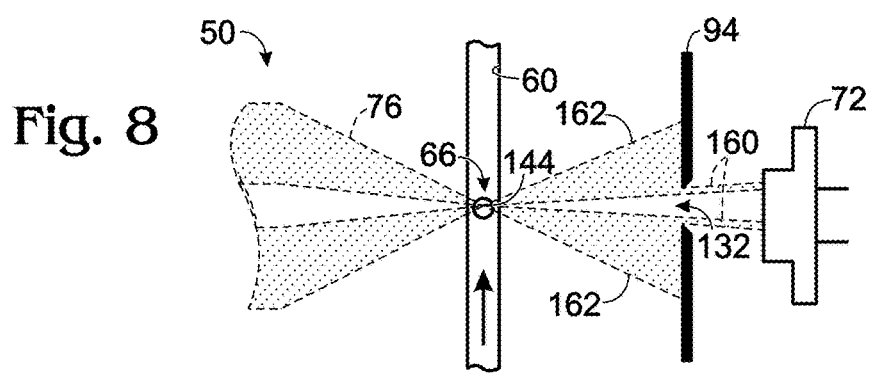
Figure 9:
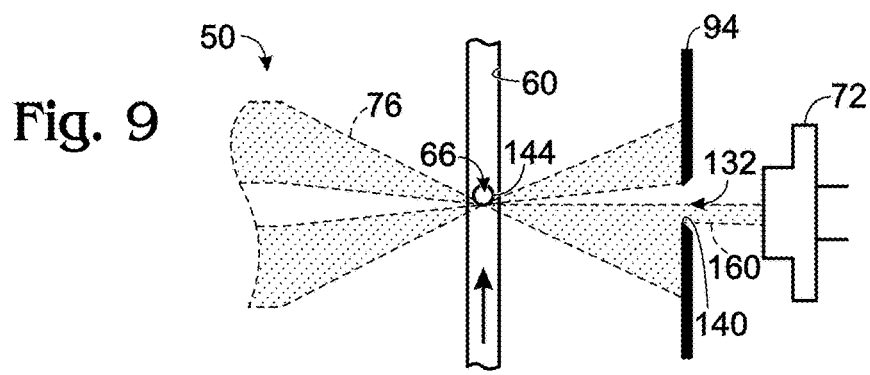

FIGS. 6-9 show exemplary deflection of light within detection and processing system 50 as a particle (e.g., a droplet 144) passes through irradiation zone 66. In FIG. 6, the entire droplet is outside of irradiation zone 66. No deflected light reaches deflection detector 72. In FIG. 7, a leading edge of the droplet has entered the irradiation zone, which produces deflected light 160 that enters shadow region 132 sufficiently to pass through optical slit 140 and reach detector 72. In FIG. 8, the droplet is roughly centered in the irradiation zone and produces deflected light 160 that enters shadow region 132 from both branches 162 of beam 76. (Each branch 162, also called a beam portion, may have about the same intensity if the line mask is centered on the beam.) In FIG. 9, the trailing edge of the droplet has entered the irradiation zone, producing deflected light 160 that enters shadow region 132 sufficiently to pass through optical slit 140 and reach detector 72.

Further aspects of exemplary assays with, and detection and processing systems for, droplets are described in U.S. Patent Application Publication No. 2010/0173394 A1, published Jul. 8, 2010, which is incorporated herein by reference.

II. FLUIDICS SUBSYSTEM

This section describes exemplary aspects of the fluidics subsystem and exemplary carrier fluid and particles therein.

The fluidics subsystem includes at least one channel 60 to contain and direct movement of carrier fluid and particles. The channel may have any suitable cross-sectional shape, such as circular, elliptical, polygonal, or the like. The channel may have a cross-sectional dimension that is approximately the same as or greater than the diameter of the particles. In exemplary embodiments, the channel is a microfluidic channel, namely, a channel having a cross-sectional dimension less than about 1 mm. Exemplary channels have a length that is at least about 2, 5, 10, or 20 times the minimum cross-sectional dimension of the channel. The channel may be a circumferentially-enclosed passage defined in a planar member, or may be an enclosed passage defined inside a tube (e.g., a tube with a cylindrical exterior), among others. The channel may be formed at least in part by molding, wet etching, dry etching, laser etching, machining, or the like.

The fluidics subsystem may include a source of negative pressure (a vacuum) to pull fluid along the channel, positive pressure to push fluid along the channel, or both. In either or both cases, the pressure may be created by a pump. The pump may be a positive-displacement pump, such as a syringe pump, among others. Other exemplary pumps include peristaltic pumps, rotary pumps, or the like. In other examples, the pressure may be provided by a container introduced to the system while holding pressurized gas or a vacuum.

The carrier fluid may be any suitable liquid or gas phase capable of transporting the particles along the channel. The carrier fluid and the particles both may be liquid, for example, a dispersed liquid phase encapsulated by a continuous liquid phase, as in an emulsion. Accordingly, the carrier phase may include oil, and optionally a surfactant. Suitable oils may include a fluorine-containing oil, a silicone oil, or mineral oil, or any combination thereof, among others. In other embodiments, the carrier phase may be a gas phase or a liquid phase and the particles may be solid-phase objects, the carrier phase may be a gas phase and the particles may be droplets (e.g., as an aerosol), or the carrier phase may be a liquid phase (e.g., an aqueous phase) or a gas phase and the particles may be biological cells.

Particles detected by the detection and processing system of the present disclosure may exist in any suitable phase, such as a liquid phase, a solid phase, or a combination thereof, among others. Exemplary particles include droplets, beads or other small solid-phase objects, biological cells, and the like.

Particles may have any suitable size. Generally, particles are less than about 1 mm in diameter and/or less than about 1 µL in volume. The particles may be at least about 1 µm in diameter and/or at least about 1 fL in volume.

Particles may have any suitable shape. Exemplary shapes include spherical, cylindrical, bullet-shaped, irregular, random, or the like. Droplets and other particles may have a size and/or shape sensitive to one or more parameters of the fluidics subsystem. The diameter and/or shape of the droplets may be influenced by the diameter of channel 60. The shape of the droplets may be spherical, and the droplets may have a diameter that is about the same as or less than the diameter of channel 60. In other cases, the droplets may be elongated, and may have a diameter corresponding (or not corresponding) to the channel's diameter. The shape of the droplets also may be affected by the flow rate of the carrier fluid, which may determine how much the droplets are stretched or otherwise deformed as they pass through the irradiation zone. In some embodiments, the droplets may have a surface layer that discourages deformation of the droplets, such that the droplets are relatively insensitive to deformation by the fluidics subsystem.

The particles may be photoluminescent, namely, capable of emitting light when irradiated with excitation light of the appropriate wavelength. Exemplary types of photoluminescence include fluorescence, phosphorescence, and the like. Each particle may contain a photoluminophore, which is any atom, molecule, moiety, complex, or aggregate capable of photoluminescence. Suitable photoluminophores include fluorescent dyes, quantum dots, and the like.

III. OPTICAL SUBSYSTEM

This section describes further aspects of the optical subsystem.

The optical subsystem may incorporate any suitable number of light sources, such as 1, 2, 3, 4, or more. The light sources may be operated to produce optical radiation that reaches the irradiation zone at the same time or at different times (e.g., alternately or sequentially).

Each light source may generate optical radiation of any suitable wavelength. In some embodiments, each light source or at least two light sources may emit visible light (e.g., at a different wavelength from other light sources of the system), or at least two light sources may emit different types of optical radiation (e.g., one light source may emit ultraviolet radiation and another light source may emit visible light).

The light source may incorporate at least one light-emitting element to generate light, and, optionally, one or more optical elements to collect and/or focus the generated light to form a beam. Exemplary light sources and/or light-emitting elements include electroluminescent lamps (e.g., light-emitting diodes and lasers (such as laser diodes)), high-intensity discharge lamps (e.g., a mercury arc lamp), and the like. Light-emitting diodes (LEDs) include any solid-state device that generates light by electroluminescence, including semiconductor LEDs, organic LEDs, and/or polymer LEDs, among others.

Each detector, also called an optical detector or photodetector, may include at least one photosensor configured to detect light of any suitable wavelength. The detector may be a point detector (e.g., a photodiode or photomultiplier) or an image detector, among others. Exemplary image detectors include multi-pixel photon counters (MPCC) (e.g., silicon photomultipliers (SiPM)), charge-coupled device (CCD) sensors, active pixel sensors (e.g., complementary metal-oxide-semiconductor (CMOS) sensors, N-type metal-oxide-semiconductor (NMOS) sensors, etc.), or the like. The detector detects light and creates a signal (e.g., an electrical signal) representing the detected light. The detector may convert photons into electrical current or voltage.

IV. METHODS OF PARTICLE DETECTION

The system disclosed herein may be utilized to perform a method of detecting a particle signal. The method steps presented in the section may be performed in any suitable order and combination, and may be modified by any other features and aspects of the present disclosure.

A beam of light may be generated. The beam may be generated with at least one light source and may, for example, contain visible light, optionally at least predominantly. In some embodiments, optical radiation of the light beam may be generated with at least one light-emitting diode or at least one laser.

The beam may be directed to a channel to create an irradiation zone in the channel where the beam intersects the channel. The channel may contain a carrier fluid flowing along the channel through the irradiation zone, with one or more particles disposed in the carrier fluid. Flow of the carrier fluid may move each of the particles through the irradiation zone, optionally serially. The flow of the carrier fluid may be driven by a pressure differential, which may be created by at least one pump.

The beam may be spatially filtered upstream of the channel. Spatial filtering may be performed at least in part in a focal plane of an optical element(s) of the system. The size of the beam may be restricted by spatial filtering, optionally with an elongated slit, such as an air slit, through which light of the beam passes. The slit may be arranged orthogonal to the channel (as defined by the long axis of the channel at and around the irradiation zone). The beam may be collimated upstream of the slit and focused on the slit. The beam may be collimated again at a position downstream of the site at which the beam is spatially filtered and upstream of the channel.

A transverse portion of the beam may be blocked upstream of the irradiation zone to create a shadow region. The shadow region may be created downstream of the region at which the beam is blocked. A mask may be used to create the shadow region. The mask may be disposed in a collimated region of the beam to block the portion of the beam.

The beam may be focused on the irradiation zone in the channel using an objective composed of one or more optical elements. Focusing the beam may be performed on a partially blocked region of the beam created by blocking the beam.

Light of the beam may be deflected by interaction with matter in the irradiation zone. The light may be deflected by a particle passing through the irradiation zone. The light may be deflected into the shadow region, and may be detected downstream of the irradiation zone. The particle passing through the irradiation zone may produce a temporary increase (a pulse) in the intensity of light detected in the shadow zone by a detector. The beam may be spatially filtered downstream of the channel, and upstream of the detector, with an optical slit operatively disposed in an optical path between the channel and the detector.

Photoluminescence induced by the beam at the irradiation zone may be detected. The detection of photoluminescence may be epi-fluorescence in which excitation light and emitted light share an optical path followed in respective opposite directions to and from the irradiation zone.

V. DETECTION CONFIGURATIONS FOR DEFLECTED LIGHT

This section describes exemplary configurations for detecting deflected light in detection and processing system 50 with deflection detector 72, with or without one or more optical elements located between irradiation zone 66 and the detector; see FIGS. 10-15. Each of the configurations of this example may be incorporated into any of the detection and processing systems of the present disclosure.

Light may be deflected at the irradiation zone by various mechanisms including refraction, reflection, Mie scattering, and the like. The relative contribution of each mechanism may be determined by particle size, shape, composition, etc.; carrier fluid properties; the nature of the interface between each particle and the carrier fluid; and the like. For example, in some embodiments of droplets disposed in a carrier fluid comprising oil, small angle deflection by micelles and large molecules (e.g., proteins) inside a droplet and on its surface, and light refraction and multiple reflection at the interface between the droplet and the oil, all may deflect optical radiation into the shadow region. However, the latter effects (refraction and multiple reflection) may deflect incident optical radiation by greater angles, to produce "large angle" deflection. In any event, the detection system may be configured to detect deflected light of interest from only a portion of the shadow region, to selectively include and exclude deflected light according to the deflection angle. Large angle deflection may create a uniform intensity distribution of light across the slit while small angle deflection may bleed around the slit edges. Accordingly, when small angle deflection is more informative about the particles, a portion of the large angle deflection that is located more central to the shadow region can be selectively excluded.

Alternatively, small angle deflection closer to the edges of the shadow region can be selectively excluded when large angle deflection is more informative about the particles. With this approach, the background level of the deflection signal may be reduced to increase the sensitivity of the detection and processing system.

Figure 10:
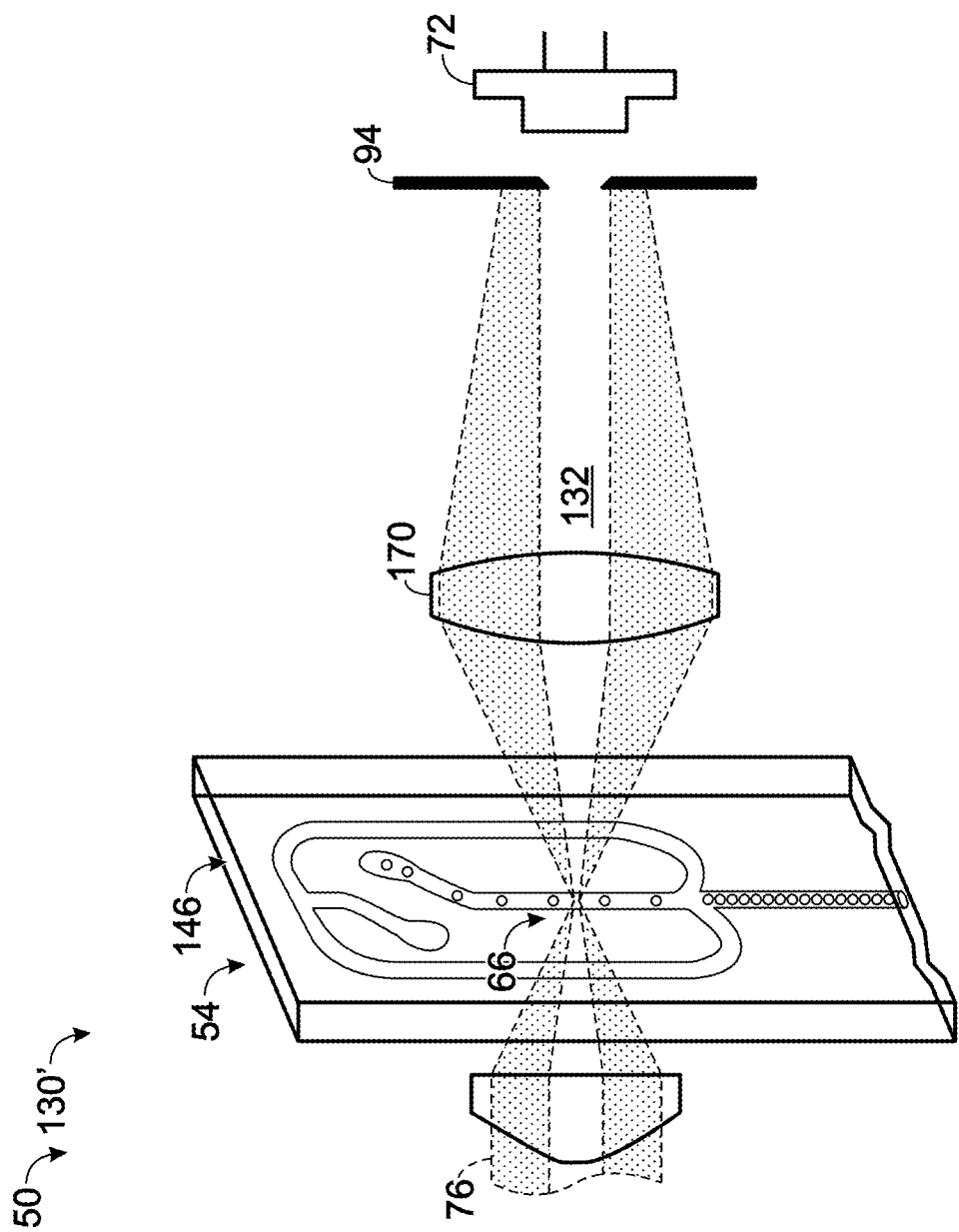
FIG. 10 is a modified version of the detection and processing system of FIG. 4 created by addition of a relay lens to focus deflected light and move an image plane of the mask farther from the channel, in accordance with aspects of the present disclosure.

FIG. 10 shows a modified version 130' of detection and processing system 130 of FIG. 5. System 130' adds a relay lens 170 between irradiation zone 66 and deflection detector 72. The relay lens may be located in a focal plane of mask 90 and re-images mask 90 to a greater distance from the irradiation zone (also see FIG. 5). Accordingly, slit-forming element 94 is located in an image plane of the mask at a position farther from the irradiation zone, which may be more convenient if space within system 50 near the irradiation zone is limited, and may increase contrast between the dark image of the mask and the area illuminated adjacent the image by beam 76. In some embodiments, the aperture of relay lens 170 may be reduced to exclude the beam and, optionally, deflected light near opposite edges of the shadow region, to selectively exclude light deflected by only a small angle. Alternatively, the aperture of relay lens 170 may be increased such that a greater amount of large angle deflection is detected, optionally predominantly. In some embodiments, the relay lens may have an aperture that renders slit-forming element 94 unnecessary.

FIG. 11 shows a fragmentary view of detection and processing system 50 of FIG. 1, taken around flow channel 60 and deflection detector 72. The configuration of FIG. 11 is presented here as a reference for comparison to the modified configurations of FIGS. 12-15.

FIG. 12 shows a modified version 50a of the detection and processing system of FIG. 1 with reduced detection of small angle deflection. System 50a has a slit-forming element 94a at the same position along the optical path as element 94 of system 50, namely, in the image plane of mask 90 (see FIG. 1), but defines a narrower optical slit 140a. Accordingly, the width of the slit may be adjusted to reduce background.

FIG. 13 shows yet another modified version 50b of detection and processing system 50. System 50b replaces detector 72 with a detector 72b having a smaller photosensitive area 138b. Area 138b may be located in the image plane of mask 90 (see FIG. 1), in place of optical slit 140 (compare with FIG. 11). The photosensitive area may be sized and positioned such that no portion of beam 76 is incident on area 138b (or detected). Instead, only light deflected in irradiation zone 66 can reach area 138b and be detected. The size and aspect ratio of area 138b may be selected to at least generally match that of the shadow region in the image plane of the mask. For example, area 138b may be elongated parallel to optical slit 86 and/or parallel to a line of mask 90. Area 138b may have an aspect ratio of at least about 5:1, or 10:1, among others. The width of area 138b may be selected to include or exclude small angle deflection.

FIG. 14 shows still another modified version 50c of detection and processing system 50. System 50c is created from system 50 by replacement of downstream optical slit 140 with a slit-forming element 94c having a pair of optical slits 140c that are parallel to one another. The pair of optical slits each may be located in the image plane of mask 90 (see FIG. 1) and may be separated by a masking region 180.

Masking region 180 reduces detection of large angle deflection. Alternatively, or in addition, another optical slit may be disposed between optical slit 140 of FIG. 11 and detector 72.

FIG. 15 shows yet still another modified version 50d of detection and processing system 50. A mask 190 is attached to the deflection detector and covers portions of photosensitive area 138. Mask 190 may be located out of the mask's image plane. Accordingly, there may be no good correlation between a point on area 138 and the deflection angle of light that can reach that point. However, extra masking or baffling of detector 72 may be effective to control some undesired light that could be present due to light deflection that occurs outside of the detection volume, for example, from an outer surface region of a channel-forming member or various imperfections.

VI. EXEMPLARY INTENSITY DISTRIBUTIONS OF DEFLECTED LIGHT

Figures 16, 17, 18:
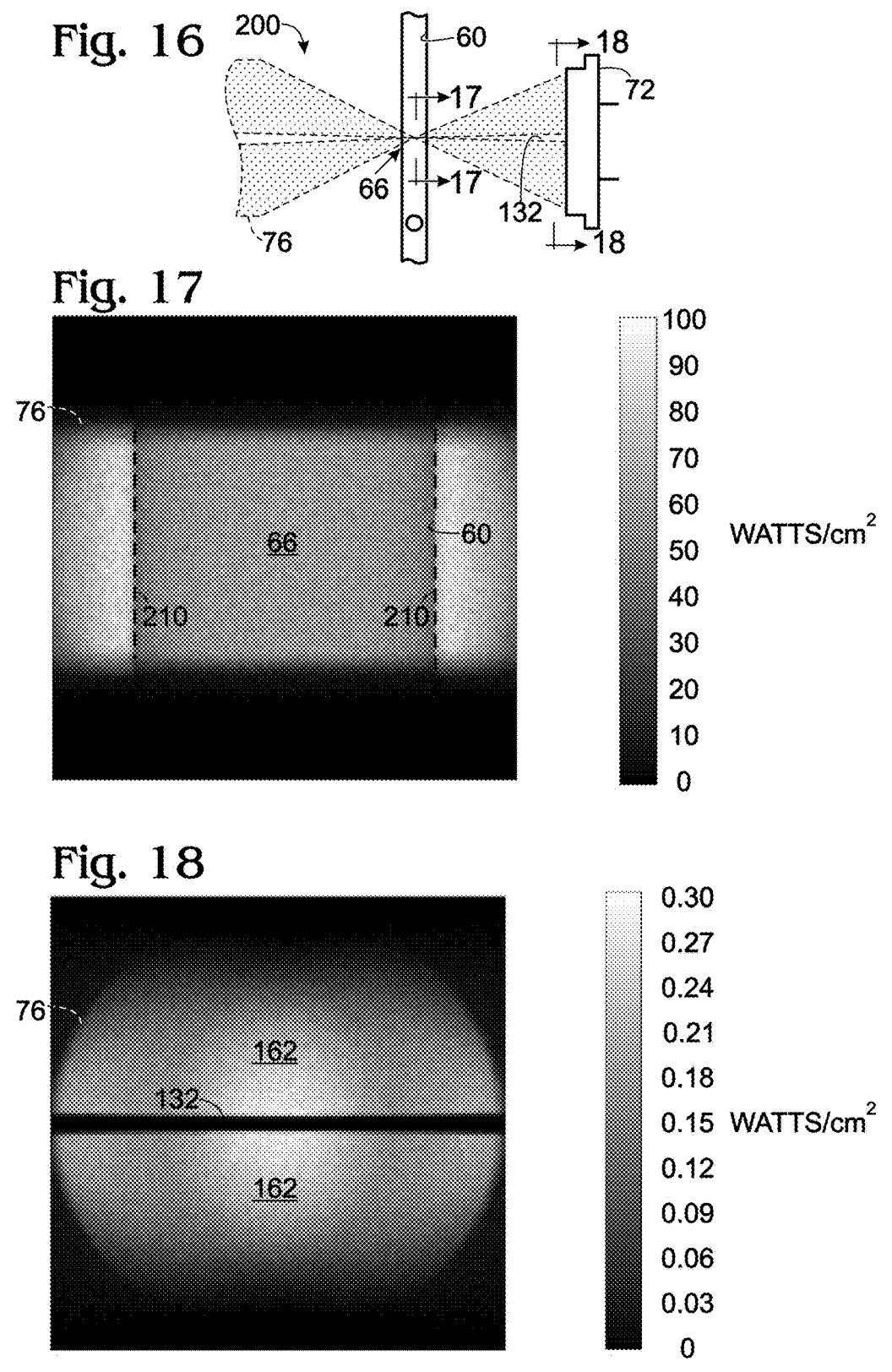

This section describes intensity distributions calculated with optical modeling software for an exemplary detection and processing system 200; see FIGS. 16-18.

FIG. 16 shows detection and processing system 200 having a deflection detector 72 sized and positioned to be illuminated by the full cross-section of beam 76. Detector 72 may be an imaging detector configured to detect beam 76 and shadow region 132. Light deflected into the shadow region may be detected as an increased intensity for image pixels representing the shadow region.

FIG. 17 shows a calculated intensity distribution of light in irradiation zone 66 of detection and processing system 200, in a plane orthogonal to the optical path of the beam and bisecting the irradiation zone. The intensity distribution was calculated with Zemax® software for a 100×100 µm region of the plane. Irradiance levels within the image are defined by the scale to the right of the image. Opposite wall regions 210 of channel 60, which delineate part of the irradiation zone, are indicated with dashed lines.

FIG. 18 shows a calculated intensity distribution of light detected by detector 72 of detection and processing system 200. The intensity distribution was calculated with Zemax® software for a 2×2 mm square region of the detector. Irradiance values within the image are defined by the scale to the right of the image. Beam 76, shadow region 132, and separate beam portions (branches 162) of the beam are indicated.

VII. DETECTION AND PROCESSING SYSTEM EMBODIMENT

Figure 19:
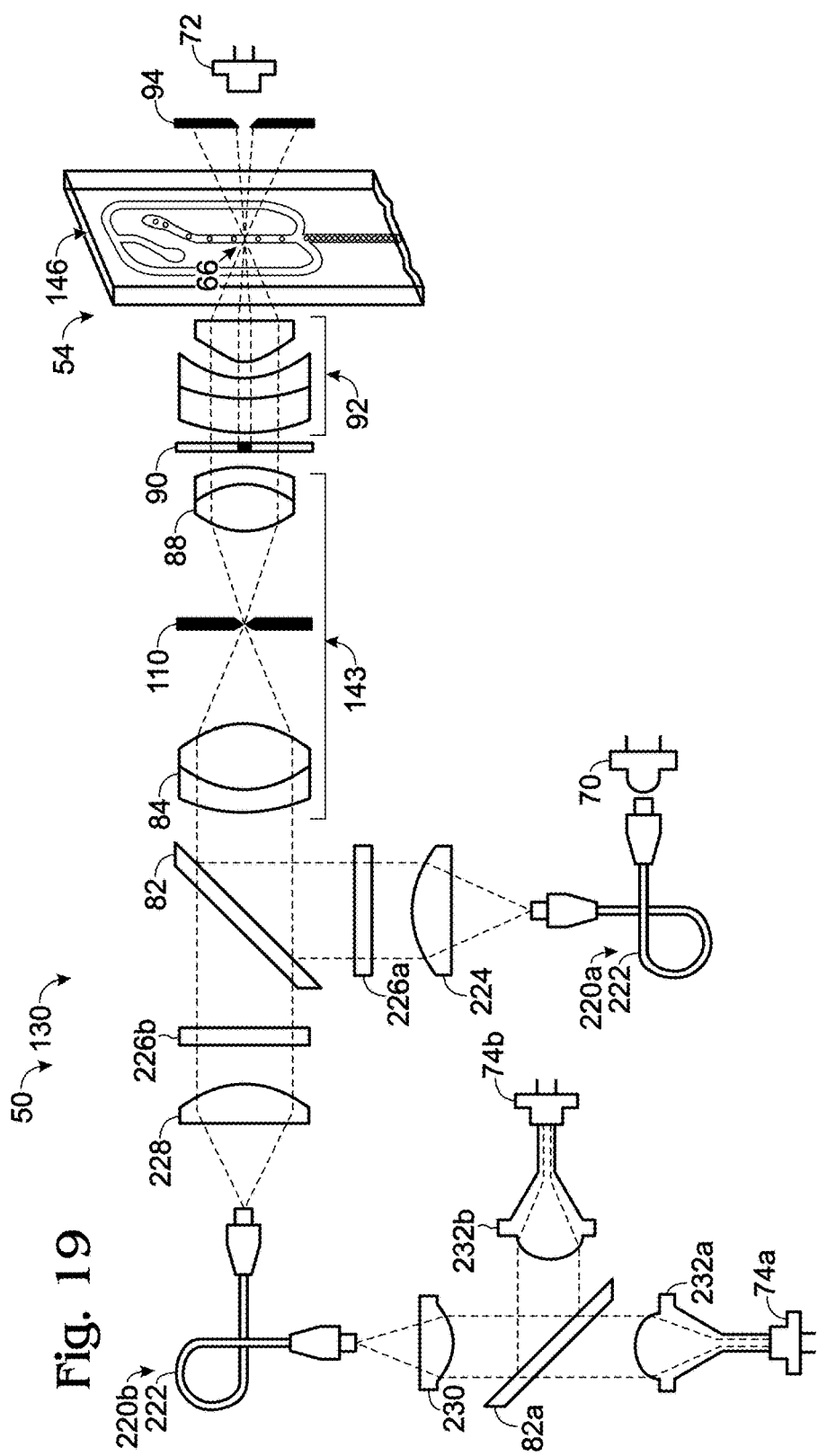
FIG. 19 is a more complete view of the detection and processing system of FIG. 5, with the view including a light source and a pair of photoluminescence detectors.

This section describes further aspects of detection and processing system 130; see FIG. 19 (also see FIG. 5).

Detection and processing system 130 has a light source 70 (e.g., an LED) and a pair of photoluminescence detectors 74a, 74b each optically coupled to spatial filter 143 and objective 92, in part, by a light guide 220a or 220b. Each of the light guides includes an optical fiber 222 that allows the optical paths for excitation and emission to bend, as needed.

Excitation light produced by light source 70 passes, in order, through light guide 220a, a collimating lens 224, and a spectral filter 226a. The excitation light then is reflected toward spatial filter 143 by a beam splitter 82 (here, a long-pass mirror), and propagated through objective 92 and irradiation zone 66, for excitation of a photoluminophore(s) therein and deflection.

Light emitted from irradiation zone 66, as photoluminescence induced by the excitation light, travels in reverse through objective 92, spatial filter 143, beam splitter 82, a spectral filter 226b, a focusing lens 228, light guide 220b, and a collimating lens 230. A portion of the collimated, emitted light then passes through a beam splitter 82a to a focusing light guide 232a and detector 74a. Another portion of the collimated, emitted light is reflected by beam splitter 82a to focusing light guide 232b and detector 74b.

Detection and processing system 130 may incorporate one or more additional light sources and/or one or more additional photoluminescence detectors. Accordingly, the detection and processing system may be configured to detect photoluminescence in only one channel with one detector, at least two channels with two detectors (as shown in FIG. 19), or three or more channels with three or more detectors, among others.

VIII. EXEMPLARY DEFLECTION AND PHOTOLUMINESCENCE SIGNALS

Figure 20:
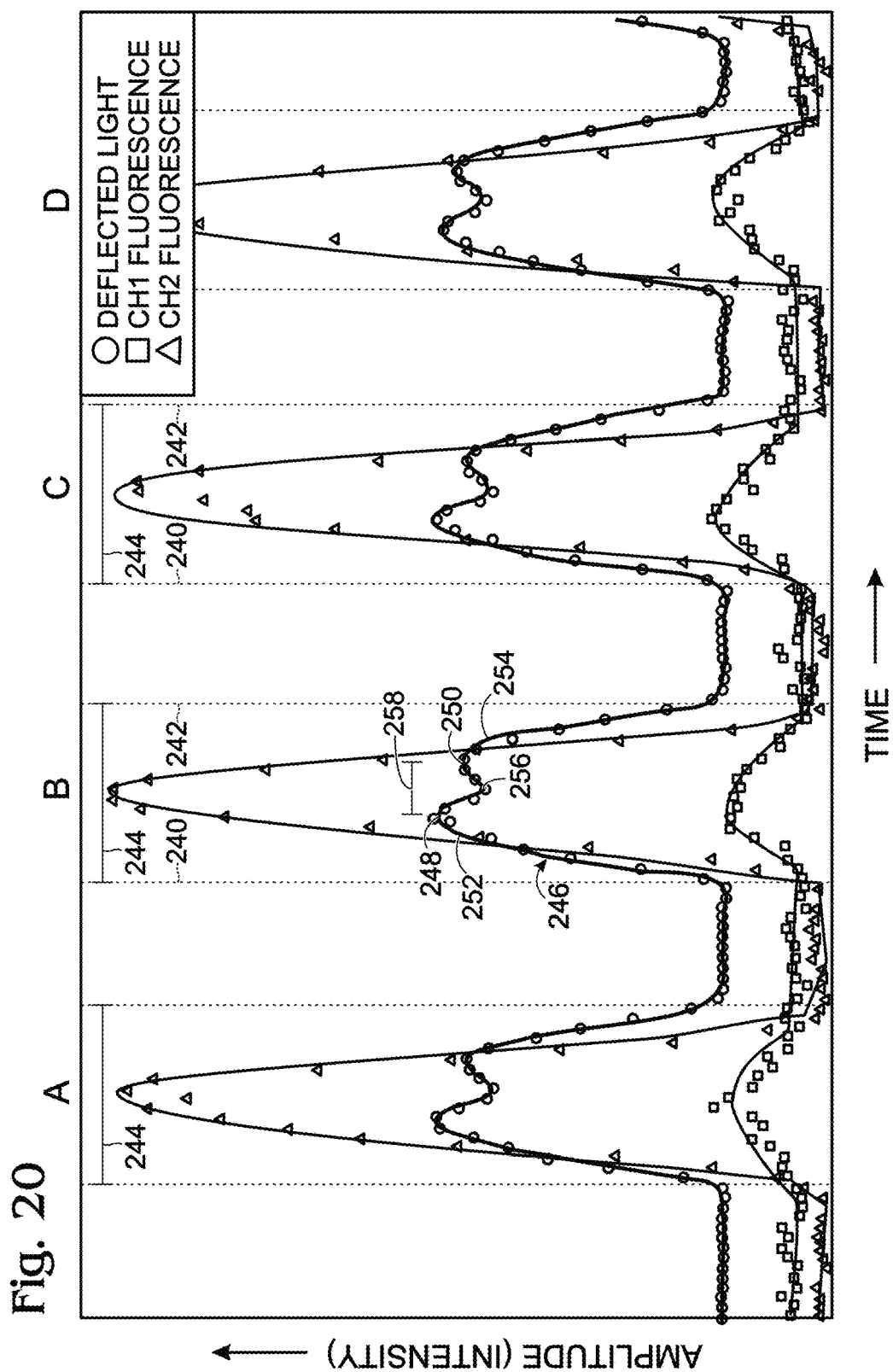
FIG. 20 is a graph of the intensity of deflected light and fluorescence detected with a working model of the detection and processing system of FIG. 19 as a function of time from a series of droplets traveling through the irradiation zone of a channel.
Figure 21:
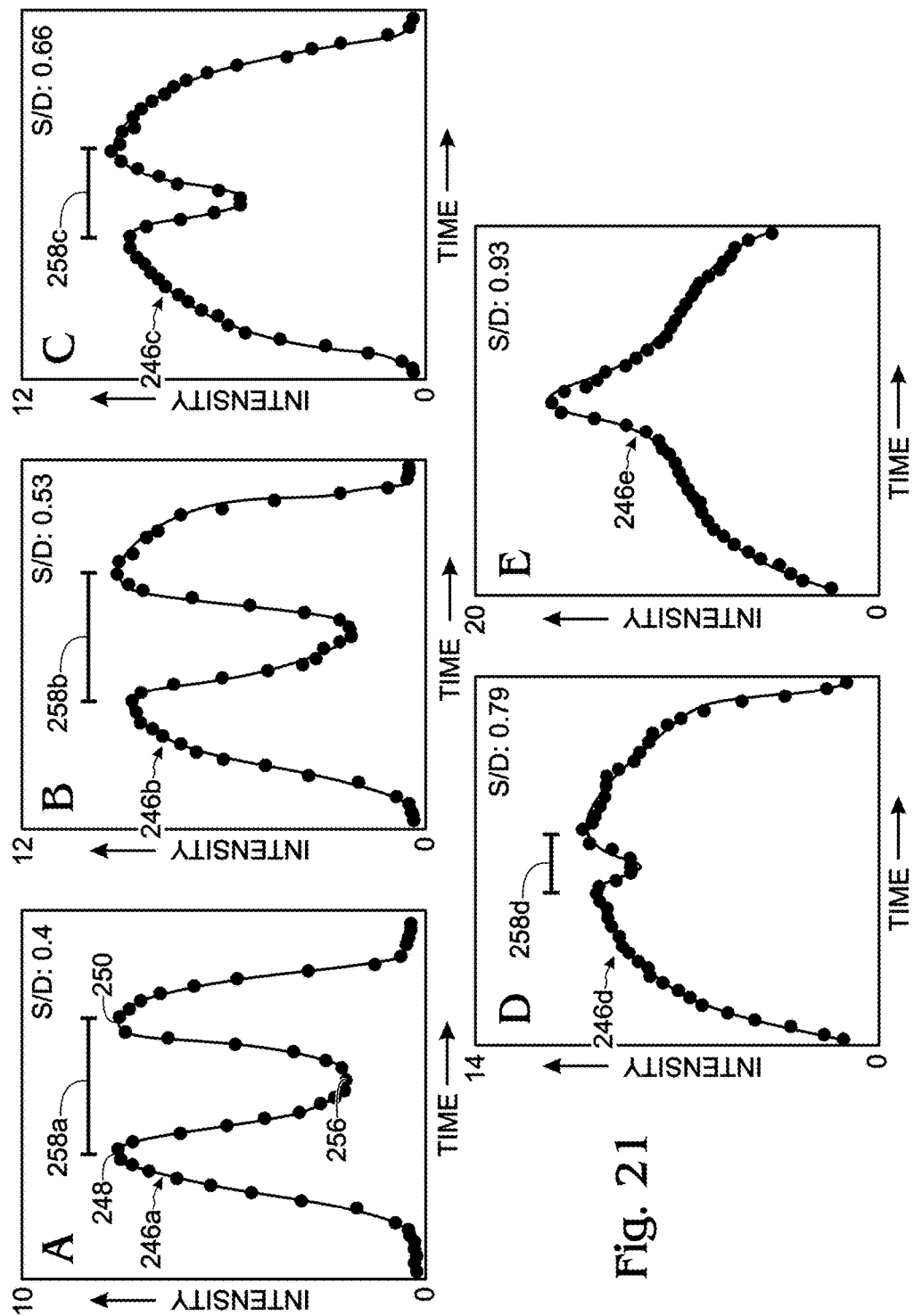
FIG. 21 is a series of graphs (A-E) showing exemplary droplet waveforms detected from droplets of the same size but with different projected widths of an optical slit located upstream of the irradiation zone in an exemplary detection and processing system.

This example describes exemplary deflection and photoluminescence signals collected from particles in the form of droplets with a working model of detection and processing system 130; see FIGS. 20 and 21.

Droplets containing a pair of fluorescent dyes were generated. The dyes emit light that is detectable with detectors 74a and 74b, respectively (see FIG. 19). The signals registered by detectors 74a and 74b are designated as channel 1 (CH1) and channel 2 (CH2) fluorescence, respectively, in FIG. 20. A deflection signal was detected by detector 72 synchronously with detection of the signals of the two fluorescence channels by detectors 74a and 74b. The intensity (amplitude) of each signal is plotted as a function of time for droplets passing through the detection volume. Portions of the signals representing four well-separated droplets are indicated by the letters A, B, C, and D, in FIG. 20.

FIG. 20 shows the deflection signal rising from baseline to a first local maximum as the leading region of each droplet enters the irradiation zone, indicated by a dashed line at 240, and returning to baseline from a second local maximum as the trailing region of the droplet exits the irradiation zone, indicated by a dashed line at 242, to define a transit interval or span 244 for the droplet. Variations in the deflection signal caused by the droplet during the transit interval create a droplet waveform 246 having a characteristic signature. The waveform includes at least one peak (i.e., a local maximum) and may, as shown, include a leading peak 248 (a first local maximum (a first height)) and a trailing peak 250 (a second local maximum (a second height)) to form a double peak (two local maxima). The waveform may have a signature characteristic of a droplet or other particle, as defined by one or more features of the waveform. Peaks 248, 250 may be created by corresponding leading and trailing regions of the droplet (and corresponding waveform), particularly a pair of humps 252, 254 formed by the leading and trailing regions of the droplet. The humps may join one another at a valley 256 (a local minimum) located temporally intermediate the pair of peaks. Any suitable characterizing value(s) calculated from the waveform(s) and/or features thereof may contribute to analysis of droplet size, droplet shape, and/or flow velocity of fluid through the irradiation zone. The characterizing values of a waveform may include the width of the waveform. The width may be measured at any suitable position between a pair of time points of the waveform and may correspond to a time interval calculated as a difference between the time points. The time points may be located at the same amplitude (height) of the deflection signal, at baseline, at a fraction (e.g., one-half) of the maximum amplitude or waveform height, or based on a characteristic amplitude of the waveform, among others. The characterizing values also or alternatively may include a width of each waveform measured as a separation value 258 corresponding to a temporal interval between the peaks within the waveform, or the like. The characterizing values also or alternatively may include a relative size (height and/or width) of the leading and trailing regions of the waveform relative to one another, a ratio of a peak or waveform height and the local minimum between peaks, a period between successive waveforms, and/or the like.

FIG. 21 shows a series of graphs (A-E) plotting a deflection signal detected from droplets of the same size (120 μm diameter) with respect to time for different widths of upstream optical slit 86 in detection and processing system 130 (also see FIGS. 5 and 19). The projected width of slit 86 at irradiation zone 66 was respectively 48, 64, 79, 95, and 111 μm for the signals shown in graphs A to E. A ratio (S/D) of projected slit width (S) to droplet diameter (D) is presented in the upper right corner of each graph. More generally, this ratio may be described as a ratio of detection volume size to average particle size, where the detection volume size and the particle size are respective characteristic dimensions of the detection volume and an average particle measured parallel to the direction of travel of particles through the detection volume. The time scale is the same for each of the graphs, and the intensity scales use the same arbitrary unit of measurement.

An exemplary droplet waveform 246a-246e detected for a single droplet passing through irradiation zone 66 is shown for each projected slit width. Separation values 258a-258d defined by peaks 248 and 250 of each waveform are indicated above each waveform. The shape of the waveforms can change dramatically with varying slit width as shown. The two humps produced by a narrower slit 86 in graphs A to C become poorly resolved in graph D and then merge to produce a single peak in graph E. Accordingly, selection of a proper slit width may allow generation of a more informative waveform. A narrower slit may produce a waveform with a deeper valley 256 (a lesser local minimum) (compare graphs A to D), but reduces the amount of deflected light detected. In other experiments, the projected slit width was kept constant and the size of droplet was varied. The shape of the deflection waveforms detected, as the droplet diameter was decreased, followed the trend of FIG. 21 and in the order shown. In other words, the two humps merged into one when the droplet size was reduced sufficiently. Accordingly, the ratio of projected slit width to droplet diameter can affect the waveform shape and may be selected to provide sufficient signal relative to noise, while still producing a waveform with sufficient separation between peaks. In exemplary embodiments, the ratio of detection volume size to particle size (as defined above) may, for example, be or be about 0.3-1.2, 0.4-1.0, 0.5-0.9, 0.5-0.8, or 0.6-0.8, among others. In some embodiments, the ratio may be less than or less than about 1.5, 1.2, 1.0, 0.8, or the like.

The droplets of FIG. 21 were formed in the presence of a skin-forming protein, BSA, and were heated to create an interfacial skin at the interface between each "skinned" droplet and the surrounding carrier phase. Similar experiments also were performed with droplets of about the same volume as in FIG. 21, but lacking an interfacial skin. These "skinless" droplets were more deformable and produced a two-peak waveform for each of the projected slit widths shown in FIG. 21. The experiments indicate that an acceptable or suitable ratio of detection volume size to particle size may vary with the composition of an emulsion, flow rate through the irradiation zone, diameter of the irradiation zone, and/or the like.

IX. OVERVIEW OF ASSAYS WITH PARTICLES

This section provides an overview of exemplary methods, such as digital assays, performed with particles, such as droplets; see FIG. 22. The assays described in this section may be performed at least in part with detection and processing system 50 (see Section I and FIG. 1), and any of the signal processing steps may be performed by an algorithm with a processor.

FIG. 22 shows an exemplary method 280 of particle analysis. The steps presented for method 280 may be performed in any suitable order and combination. In other words, any single step or combination of two or more steps of method 280 is optional and may be omitted. Method 280 may be modified by or combined with any other suitable aspects of the present disclosure.

Particles may be obtained, indicated at 282. The particles may be obtained by any suitable procedure(s) or mechanism(s), such as isolation, chemical reaction (e.g., cross-linking), fluid dispersal, and/or the like. The particles may include at least one analyte, which is any substance undergoing analysis. The analyte, may, for example, be a nucleic acid (e.g., a polynucleotide, such as DNA or RNA, or a sequence thereof), a protein, a peptide, an amino acid, a macromolecular complex, a lipid, an atom, a metal, a hormone, a virus particle, a biological cell, and/or the like. Each analyte may be present at "partial occupancy" in a set of particles obtained, meaning that each particle of only a subset of the particles of the set contains at least one copy or molecule of the analyte. In some embodiments, the particles may be obtained by forming droplets, which may be produced by partitioning a continuous phase, such as a continuous aqueous phase. The droplets may be substantially the same size (monodisperse). Droplets may be formed by any suitable mechanism, such as flow focusing, shearing, ejection into air, sonication, or the like.

A reaction may be performed in the particles, indicated at 284, to enable detection of the presence of each analyte. The reaction may be performed at the surface and/or in the interior of particles. The reaction may, for example, be an enzyme-catalyzed reaction. In exemplary embodiments, the reaction includes an amplification reaction, which may amplify a target sequence of nucleic acid. Amplification may or may not be performed isothermally. In some cases, amplification may be encouraged by heating the particles and/or incubating the particles at a temperature above room temperature, such as at a denaturation temperature (e.g., greater than about 90 degrees Celsius), an annealing temperature (e.g., about 50-75 degrees Celsius), and/or an extension temperature (e.g., about 60 to 80 degrees Celsius), for one or a plurality of cycles. In some examples, the particles may be thermally cycled to promote amplification by a polymerase chain reaction and/or ligase chain reaction, among others. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

Signals may be detected from the particles, indicated at 286. The signals may include a deflection signal and at least one photoluminescence signal. Each photoluminescence signal may have an amplitude (e.g., an intensity) corresponding to the level (e.g., presence or absence) of one or more analytes in individual particles. Each photoluminescence signal may be detected from a label contained by the particles. The label may, for example, be provided by a dye, which may be photoluminescent (e.g., fluorescent).

The deflection and photoluminescence signals may be detected by two or more detectors, such a respective detector for the deflection signal and each photoluminescence signal(s). Each detector may detect a signal by detecting light received from the irradiated detection volume (and the fluid/particles therein) and creating a signal representative of the detected light. In other embodiments, the detector may, for example, detect a different type of radiation, an electrical property, a magnetic property, or the like. Detection and signal creation collectively, whether or not performed optically, are described herein as signal detection.

Each photoluminescence signal may be detected from a label contained by each of the particles. The label may, for example, be an optically detectable label, such as a photoluminophore (e.g., a fluorophore or a phosphor), among others. Accordingly, the photoluminescence signal may represent an intensity of light emitted from particles. Exemplary labels suitable for amplification reactions include fluorophores attached to oligonucleotides, intercalating dyes, and the like.

Each signal may be detected from a stream of fluid passing through an irradiation zone (a detection volume) of a detection system. The deflection and photoluminescence signals may be detected from the detection volume over the same time period. Individual time points of the deflection signal may or may not be collected synchronously with individual time points of the photoluminescence signal. Accordingly, deflection signal time points may or may not be collected at the same frequency as photoluminescence signal time points, and with or without a temporal offset. The time points may, for example, be collected by digitizing an analog detector signal with an analog-to-digital converter at any suitable sampling frequency.

Particle waveforms in the deflection signal may be identified, indicated at 288. Each waveform may correspond to an individual particle, and may span a time interval corresponding to the size of the particle. The waveform may have a single local maximum (e.g., above a threshold) or at least a pair of local maxima (e.g., each above a threshold), which may be temporally separated from one another by at least one local minimum (e.g., below a threshold). The waveforms may be identified in real time, namely, as the deflection signal is being detected, or may be identified after detection of the deflection signal has been completed for a set of particles. The waveforms identified may be single-peak waveforms, double-peak waveforms, or a combination thereof, among others. In some embodiments, the waveforms may be identified by a state machine, as described further in Section X. The state machine may be configured to identify only double-peak waveforms, only single-peak waveforms, or both double-peak and single-peak waveforms, among others. In any event, each waveform may be identified based on any suitable criteria, for example, using any of the criteria described for droplets in Section VIII.

At least one characterizing value may be obtained (e.g., calculated) for individual waveforms, indicated at 290. The at least one characterizing value may include any of the characterizing values described in Section VIII. In some embodiments, the characterizing value may be a width value. The width value may be calculated as a temporal difference between any suitable pair of time points of each waveform. The time points of the waveform may have the same amplitude (e.g., intensity) as one another, or different amplitudes (e.g., intensities). In some embodiments, the amplitude(s) at which the width value is calculated may be different among the waveforms, and may be specific to each waveform. For example, in some embodiments, the width value may be calculated at an amplitude that is proportional to a characteristic amplitude of each waveform. The characteristic amplitude may be a maximum amplitude of the waveform, an amplitude at which the waveform (or a region thereof) has a maximum slope, or the like. The region of the waveform having a maximum slope may be a leading region (between baseline and the first or only peak), a trailing region (between the last (e.g., second) or only peak and baseline), or a region intermediate the leading and trailing regions of the waveform. In some cases, the width value may be a separation value calculated by finding a temporal difference between two local maxima of a double-peak waveform. In some embodiments, the local maxima may be defined by fitting a pair of curves to points of the double-peak waveform (e.g., points forming a pair of pulses/protrusions (e.g., humps)), as described further below in Section X.

Particles (and corresponding waveforms/amplitudes) may be excluded based on the characterizing values and/or one or more other criteria, indicated at 292. The particles and data therefor may be excluded from further consideration. The particles may be excluded based on their corresponding characterizing values. The step of excluding excludes one or more particles and their corresponding amplitudes/waveforms from subsequent steps of the method. In some embodiments, each of the characterizing values may be compared to a reference, which may be predefined or may be calculated from the characterizing values. In some embodiments, the reference may be an average of the characterizing values. Each characterizing value deviating from the reference by more than a threshold (i.e., each value outside a range) may trigger exclusion of a particle and its corresponding amplitude(s) and/or waveform from subsequent steps. The threshold or range may be predefined before the characterizing values are calculated, or may, for example, be determined based on the distribution of the characterizing values relative to an average of the characterizing values. In some embodiments, the threshold may correspond to a standard deviation from the average of the characterizing values, such as corresponding to the standard deviation multiplied by a constant (e.g., an integer, such as 1, 2, or 3, among others).

Boundaries in each photoluminescence signal for individual particles may be defined, indicated at 294. The boundaries for each individual particle may be a leading boundary and a trailing boundary defined along a time axis by applying a temporal offset to each of the two time points at which the characterizing value (e.g., the width value) of the waveform is calculated. The temporal offsets may be the same for each waveform, may be of the same temporal size within the waveform, and/or may be in opposite directions along the time axis from one another within the waveform. For example, the leading and trailing boundaries, respectively, of a waveform may be calculated by subtracting a time value from the leading time point used for the width value, and by adding the same time value to the trailing time point used for the width value. In some cases, the same time value may be respectively added to and subtracted from the time points of the leading and trailing peaks of the waveform, to obtain the boundaries, as described further below in Section X. Each pair of leading and trailing boundaries may be defined from a temporally corresponding waveform, and then applied to the temporally corresponding portion of each photoluminescence signal.

Amplitudes for individual particles may be obtained from each photoluminescence signal, indicated at 296. Each amplitude may represent a portion of the photoluminescence signal that temporally overlaps a waveform, with any suitable amount of overlap. Each amplitude thus may be associated with and correspond to one of the waveforms of the deflection signal. The amplitude may be obtained directly from the photoluminescence signal or may be calculated, such as by subtracting background, integrating, and/or adjusting, among others. Accordingly, in some embodiments, each amplitude may represent an integrated portion of a photoluminescence signal, such as an integrated intensity, optionally with background subtracted. Sections of the photoluminescence signal temporally corresponding to the waveforms of the deflection signal may be integrated to obtain respective integrated amplitudes (i.e., integrated intensities). Integration may include summing values (e.g., intensity values) of points of a photoluminescence signal, over a span from the leading boundary to the trailing boundary, inclusive or exclusive of a point, if any, located at each boundary. Accordingly, the boundaries may function as integration boundaries. In some embodiments, individual amplitudes (e.g., a maximum intensity of the photoluminescence signal over the time span of a temporally corresponding waveform) may be obtained directly by retrieval from the photoluminescence signal, without integration or other manipulation.

An analyte content of individual particles may be assigned using amplitudes, indicated at 298. The analyte content may indicate whether a given particle is positive (contains at least one copy/molecule) or negative (contains no copies/molecules) of a single analyte or two or more different analytes, and/or may indicate a number of copies/molecules (e.g., an integral number of copies/molecules) of each analyte present in the given particle. Amplitudes, optionally after at least one adjustment or correction, may be compared to at least one threshold to assign an analyte content to each particle. In some embodiments, amplitudes from two or more different photoluminescence signals detected from particles at the same time (e.g., detected at two or more different wavelengths) may be compared to a plurality of thresholds to assign analyte content to the particles. Assignment may include assigning individual particles as having two or more possible analyte contents (e.g., either positive for analytes A and B or positive for analyte C).

Particles may be enumerated based on analyte content, indicated at 300. Only particles not excluded at step 292 may be considered during the step of enumeration. The process of enumeration may include determining a number of non-excluded particles having a given analyte content (e.g., particles that are positive or that are negative for a particular analyte). The given analyte content may be defined for a single analyte or two or more analytes, and may, for example, be defined as a presence (positive) or absence (negative) or a number of analyte copies for each analyte. In some embodiments, a number of non-excluded particles that are positive for each analyte may be determined, a number of non-excluded particles that are negative for the analyte may be determined, or both numbers may be determined. A total number of non-excluded particles also may be determined, and the total number may correspond to the sum of the number of non-excluded particles positive for the analyte and the number of non-excluded particles negative for the analyte.

A concentration of an analyte may be determined, indicated at 302. The concentration may be calculated using at least one number of particles determined by the step of enumerating (step 300). In exemplary embodiments, the concentration may be calculated with Equation 1:

$$C_1 = -\ln(N_n/N_t) \quad (1)$$

In Equation 1, $C_1$ is concentration expressed as the average number of copies per particle), $N_n$ is the number of negative particles, and $N_t$ is the total number of particles. The ratio of $N_n$ to $N_t$ is the fraction of particles negative for the analyte. The concentration also or alternatively may be calculated with Equation 2:

$$C_2 = -\ln(N_n/N_t) \div V_d \quad (2)$$

In Equation 2, $C_2$ is concentration expressed as copies per unit volume and $V_d$ is the average volume of a particle.

Since the number of positive particles, $N_p$, is equal to the difference between $N_t$ and $N_n$, either concentration $C_1$ or $C_2$ may be calculated with $N_p$ and $N_t$. For example, the concentration per unit volume equivalently may be determined with Equation 3:

$$C_2 = -\ln(1 - N_p/N_t) \div V_d \quad (3)$$

The ratio of $N_p$ to $N_t$ is the fraction of particles positive for the analyte.

X. EXEMPLARY ALGORITHMS FOR SIGNAL PROCESSING

This section describes exemplary algorithms for processing deflection and photoluminescence signals detected from particles, such as droplets; see FIGS. 23A, 23B, and 24-31. The algorithms are described with respect to droplets and are illustrated with exemplary signals detected from droplets, but may be used to process signals detected from any suitable particles. Any suitable combination of the algorithms, or aspects thereof, disclosed in this section may be stored in a memory of detection and processing system 50 of Sections I-VIII and/or may be incorporated into any of the methods disclosed in Section IX or elsewhere herein.

Figure 23A:
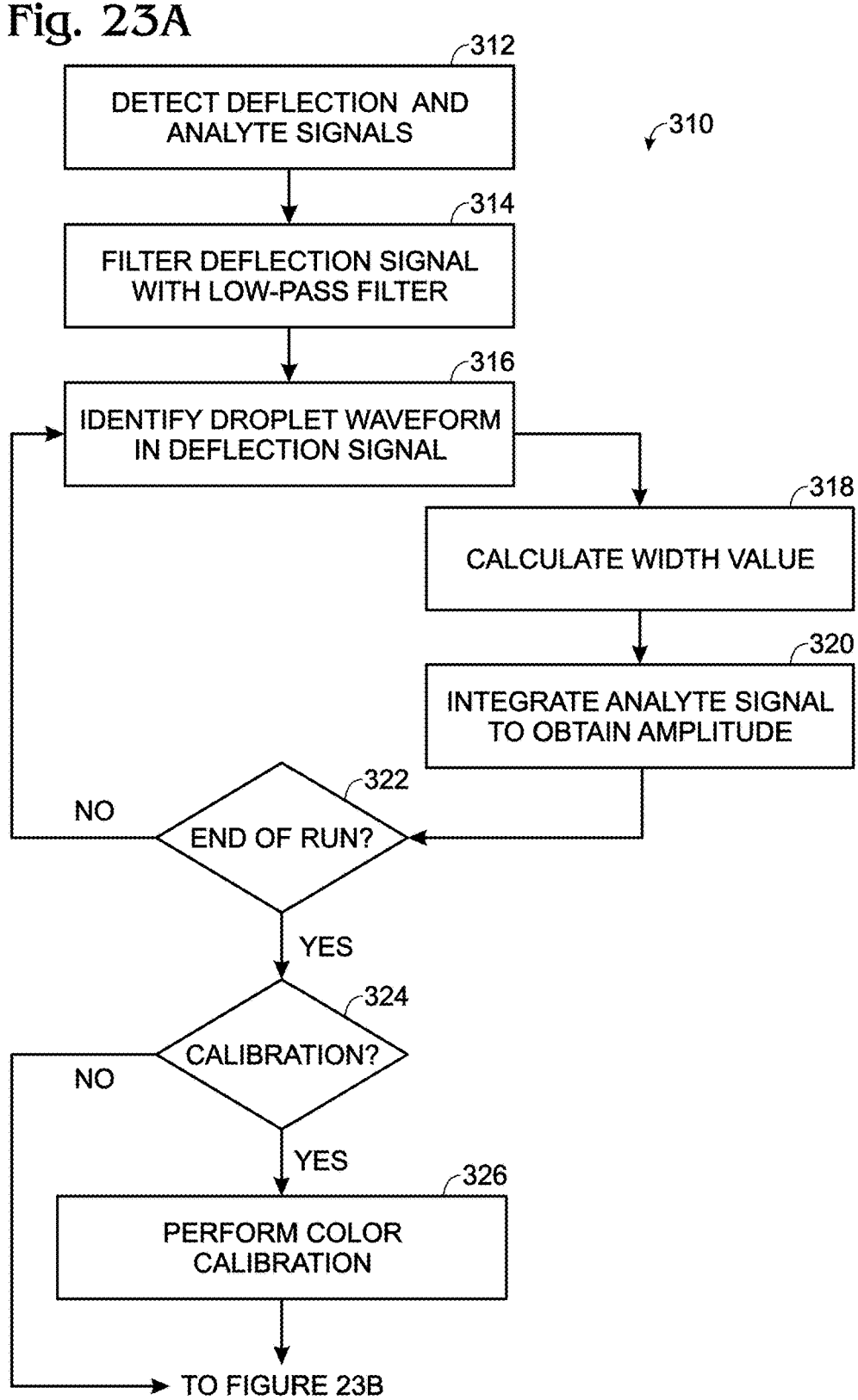
FIGS. 23A and 23B collectively are a flowchart illustrating an exemplary algorithm, and signal processing steps thereof, that may be utilized to perform a method of particle analysis according to FIG. 22.
Figure 23B:
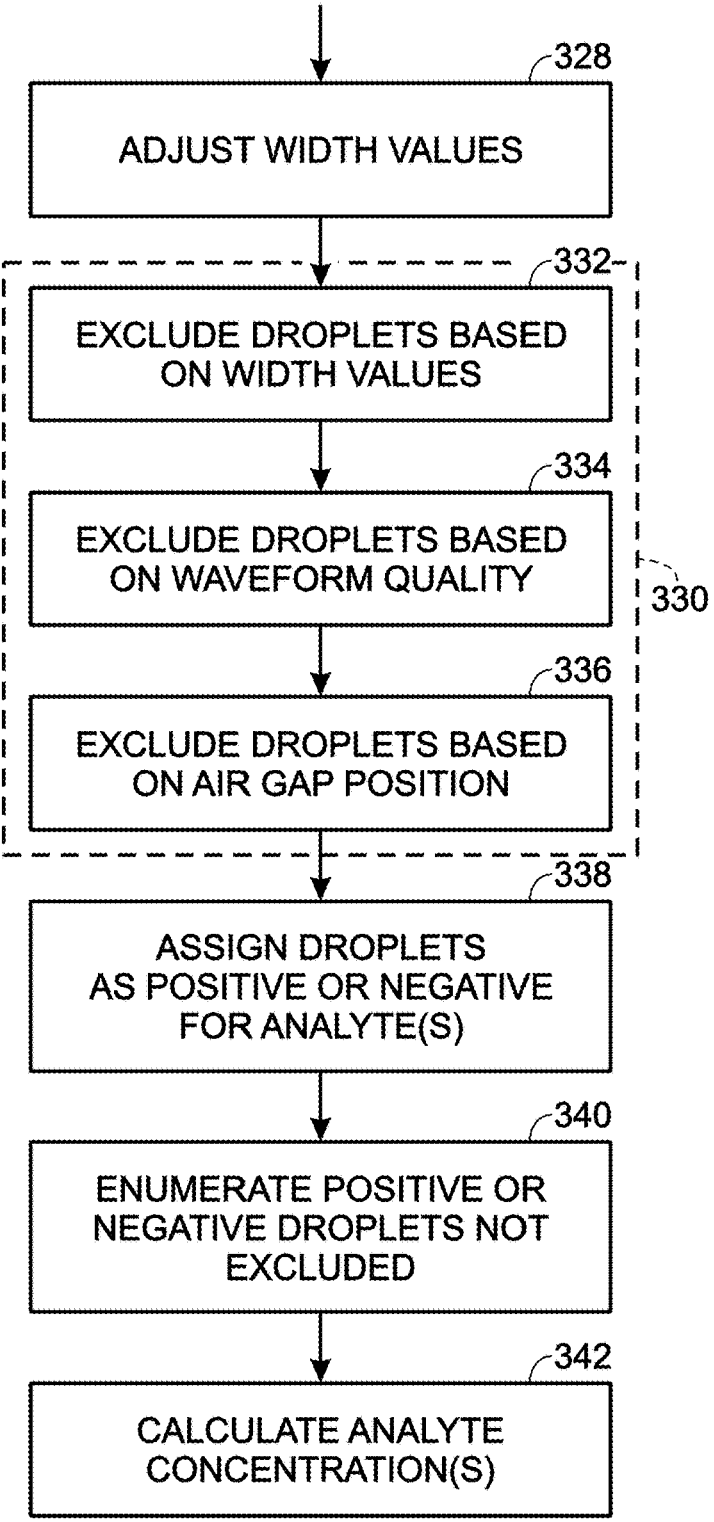

FIGS. 23A and 23B collectively show a flowchart illustrating an exemplary algorithm 310 and signal processing steps thereof that may be executed to perform a method of particle analysis (also see FIG. 22). The steps of algorithm 310 may be performed in any suitable order and combination.

A deflection signal and an analyte signal (e.g., a photoluminescence signal) may be detected, indicated at 312. Signal detection may be performed as described elsewhere herein, such as in Sections I-IX (e.g., see step 286 of FIG. 22).

The deflection signal may be filtered, indicated at 314. For example, the deflection signal may be filtered with a frequency-based filter, such as a low-pass filter (e.g., less than about 100, 75, 50, 40, 30, 20, or 10 kHz, among others). Frequency filtering may be performed on a digital or analog form of the deflection signal. The filtering may reduce noise and enable identification of droplet waveforms in the following step.

A droplet waveform may be identified in the deflection signal, indicated at 316. The deflection signal may include desired waveforms satisfying one or more conditions, such as meeting one or more criteria (e.g., having a predefined particle (droplet) signature), and also may include other waveforms that do not meet all of the criteria. The identification process can distinguish the desired waveforms from the other waveforms. Identification of a waveform having a particle signature may be performed as described elsewhere herein, such as in Section IX (e.g., see step 288 of FIG. 22), and further below in this section with respect to a state machine.

A width value may be calculated for the droplet waveform, indicated at 318. The width value may be calculated as described elsewhere herein, such as in Section IX (e.g., see step 290 of FIG. 22) and below in this section.

A portion (e.g., a segment) of the photoluminescence signal may be integrated to obtain an amplitude (e.g., an integrated intensity, also called an integrated intensity value), indicated at 320 (and described more with respect to step 296 of FIG. 22). The segment temporally overlaps a waveform in the deflection signal. At least part or all of the segment is detected over the same time span as at least a portion of the waveform. Integration boundaries for the segment may be defined with a temporally corresponding waveform based on features (e.g., peaks) of the waveform as described further below in this section.

A decision whether to continue identifying waveforms may occur next, indicated at 322. Algorithm 310 may decide based, for example, on whether the frequency at which droplet waveforms are being identified has changed (increased or decreased) by more than a threshold amount and/or whether one or more periods (or temporal gaps) between at least one successive pair of droplet waveforms exceeds a threshold or is outside a range, among others. If the answer is no, the algorithm may return to step 316 for identification of another droplet waveform, to form a loop. If the answer is yes, the algorithm may stop identifying droplet waveforms (step 316) and optionally may stop detecting signals (step 312) and/or stop passing droplets through the detection volume. Accordingly, step 312 may continue to be performed while steps 314, 316, 318, and/or 320 are performed cyclically, until the end of the run is detected. An end of the run may be triggered by, for example, exhaustion of an emulsion supplying the droplets, introduction of one or more air bubbles into the detection volume, an obstruction (a clog) inhibiting fluid flow through the detection volume, a mechanical error, or the like.

A decision whether to perform a color calibration may occur next, indicated at 324. If the answer is yes, the algorithm may proceed to step 326. If the answer is no, the algorithm may skip the color calibration. The algorithm may decide whether to perform the color calibration based, for example, on whether an input has been received from a user instructing the algorithm to skip the color calibration. In some cases, the user may wish to skip the color calibration in order to measure coupling constants between photoluminescence signals when using particular labels to produce the signals.

A color calibration may be performed, indicated at 326. The color calibration may correct for coupling (also called crosstalk) between different photoluminescence signals, in which at least one of the photoluminescence signals is affected by the other photoluminescence signal. The coupling may, for example, occur in an assay performed with two or more photoluminescence labels that are detectable at respective different wavelengths (i.e., in different detection channels) by different detectors. In many cases, at least one of the labels is detectable predominantly in one detection channel but also is detectable less efficiently in one or more other detection channels as crosstalk. The color calibration decouples photoluminescence signals by removing crosstalk. Accordingly, the color calibration may adjust amplitudes that have been obtained from each photoluminescence signal at step 320, and one or more subsequent steps may be performed with the adjusted amplitudes.

Width values may be adjusted, indicated at 328. More particularly, the width values calculated cyclically at step 318 for the waveforms may be adjusted to correct for fluctuations, if any, in flow rate through the detection volume during the run. The fluctuations may be detected by monitoring the deflection signal. The fluctuations generally are undesired but may be difficult to prevent completely and may occur for various reasons. If the flow rate of fluid through the detection volume increases during the run, waveforms each span a shorter time period (become narrower), and thus produce a lower width value (and a lower integrated photoluminescence amplitude). Alternatively, if the flow rate of fluid through the detection volume decreases during the run, waveforms each span a longer time period (become wider). Algorithm 310 may utilize a spline to adjust the width values. The spline may adjust temporally-grouped sets of the width values piecewise with different functions, such as different polynomial functions. For example, the width values may be replaced with a spline fit and the residuals of the fit may be used to adjust width values.

Droplets may be filtered, indicated at 330. Exemplary filtering steps that may be performed alone or in any suitable order and combination are indicated at 332, 334, and 336. Filtering interchangeably may be described as gating. The process of filtering excludes selected droplets and corresponding portions of each signal from any suitable combination of later steps performed by the algorithm. Accordingly, the process of filtering also or alternatively may be described as filtering waveforms and/or amplitudes.

Droplets may be filtered according to their corresponding width values, indicated at 332. Step 332 may be performed as described for step 292 of FIG. 22. In exemplary embodiments, the width values each may be compared to a range to exclude droplets corresponding to width values having greater than a threshold deviation (e.g., three standard deviations) from an average width value. Each amplitude corresponding to an excluded droplet thus may be excluded from one or more subsequent steps.

Droplets also or alternatively may be filtered according to the quality of temporally corresponding deflection-signal waveforms, indicated at 334. Droplets having waveforms failing to meet one or more criteria distinct from their width values, may be excluded, along with corresponding amplitudes from the photoluminescence signal. These criteria may involve a ratio of at least one local maximum and a local minimum of the waveform, a ratio of local maxima of the waveform to each other, a span of the waveform from its leading boundary to its trailing boundary, a span of the waveform from its leading boundary to its leading peak or its valley, a span of the waveform from its valley or trailing peak to its trailing boundary, whether or not the waveform is well-resolved from adjacent waveforms (i.e., starts from and returns to baseline), and/or the like.

Droplets also or alternatively may be filtered according to the position of a change in the deflection signal that meets a condition, indicated at 336. The change may, for example, be an abrupt change caused by an air gap created when an air bubble(s) enters the fluidics subsystem and travels through the detection volume, which may indicate that the emulsion supplying the droplets has been depleted. The introduction of air can cause the flow rate to change substantially and become erratic. Each deflection-signal waveform (and thus droplet) detected after the abrupt change for the rest of the run may be excluded, along with a temporally corresponding amplitude(s) from the photoluminescence signal(s).

Analyte content may be assigned, droplets may be enumerated, and at least one analyte concentration may be calculated, indicated at 338, 340, and 342. Exemplary approaches to performing these steps have been described above for steps 298, 300, and 302 of FIG. 22.

FIG. 24 shows a graph of a deflection signal 350 and fluorescence signals 352, 354 (channel 1 (CH1) and channel 2 (CH2) fluorescence) detected with a working model of the detection and processing system 130 of FIG. 19. Only a short region of each signal is shown here, to illustrate how the three signals may change when a single droplet passes through the irradiation zone of system 130. Each signal is composed of a series of time points, which may be uniformly spaced along the time axis. Each time point may be defined by a time value and a signal value. The signal value may be described as a deflection value or a photoluminescence value for the deflection signal and a photoluminescence signal, respectively. The signal value may be an amplitude expressed as an intensity, which may be expressed with or without subtraction of background. Signal values may be combined, averaged, adjusted, and/or the like to generate other signal values.

Deflection signal 350 produces a droplet waveform 246 that rises from and returns to baseline 356 in the graph. Waveform 246 has a leading peak 248 and a trailing peak 250, which are respective crests of a leading hump 252 (or pulse) and a trailing hump 254 (or pulse). Each hump may, for example, be rounded or sharp at and surrounding the crest. A valley 256 is defined temporally intermediate the peaks. In some embodiments, the waveform may have at least one additional local maximum and at least one additional local minimum. A separation value, as described elsewhere herein, may be calculated between any pair of local maxima (or a local maximum and a local minimum) of the waveform.

Photoluminescence signals 352, 354 produce respective pulses 358, 360 temporally overlapping waveform 246. In the graph, each pulse 358, 360 rises from and returns to the baseline for signals 352, 354 at about the same time as waveform 246. However, pulse 360 is much smaller than pulse 358, making the pulse difficult to characterize accurately, and, in cases, where noise is significant, difficult to reliably identify. The use of deflection waveform 246 to identify the temporal location of each droplet, allows pulse 360 to be identified and characterized with greater confidence.

Figure 25:
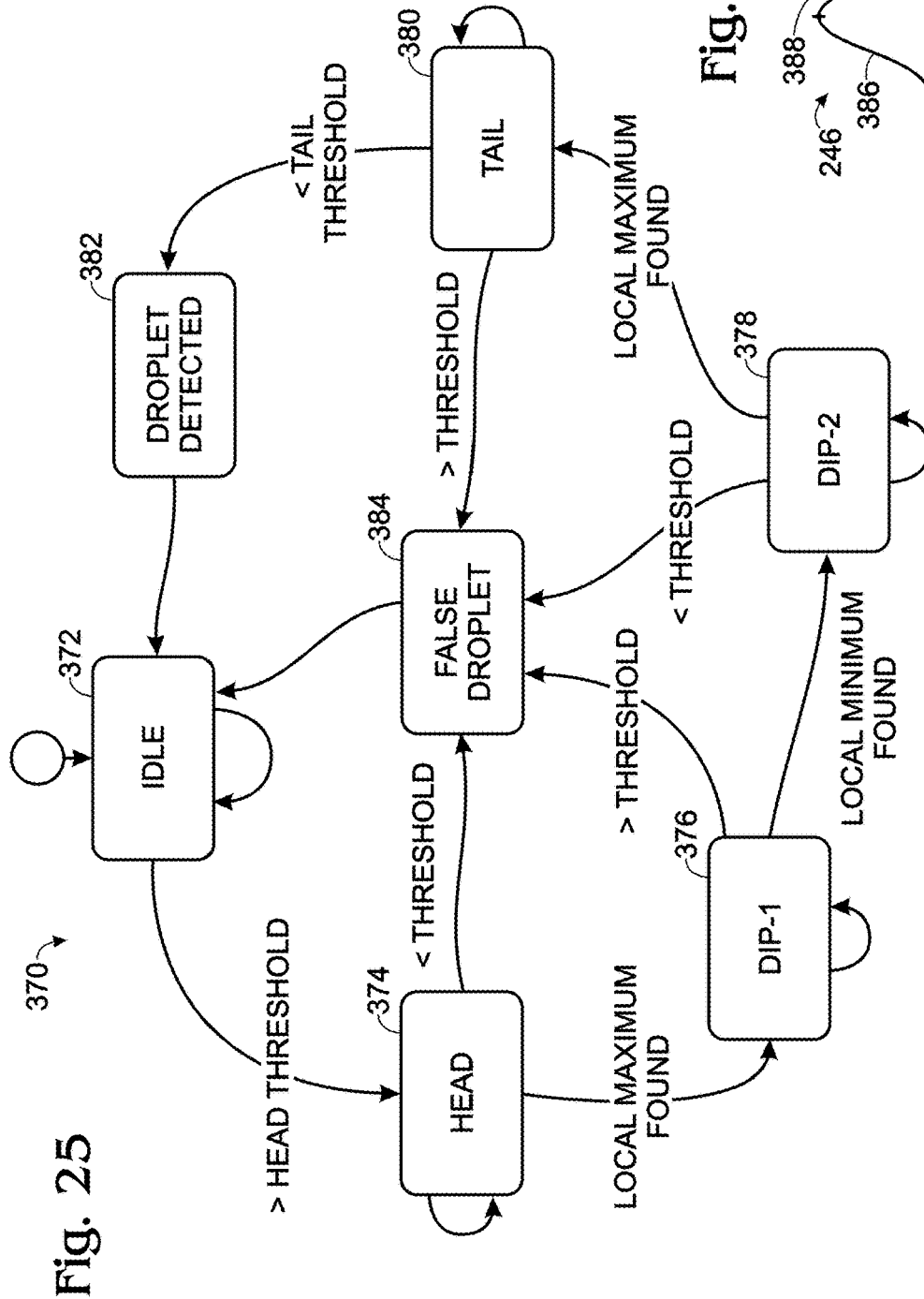
FIG. 25 is a schematic view of an exemplary state machine to identify double-peak waveforms in real time from a deflection signal as the deflection signal is being detected from particles passing through a detection volume, in accordance with aspects of the present disclosure.

FIG. 25 shows an exemplary state machine 370 to identify droplet (or other particle) waveforms present in a deflection signal. The state machine may identify double-peak waveforms in the deflection signal. As described further below in this section, the state machine also (or alternatively) may be configured to identify single-peak waveforms in the deflection signal. In any event, the waveforms may be identified in real time as the deflection signal is being detected, and may help to determine when to stop collection of the deflection signal and photoluminescence signal(s). The state machine may transform to multiple states as the state machine monitors values of the deflection signal. Exemplary states for identifying a double-peak waveform include idle 372, head 374, dip-1 376, dip-2 378, tail 380, droplet detected 382, and false droplet 384. Exemplary states for identifying a single-peak waveform may be a subset of the states used for identifying a double-peak waveform, such as the idle, head, tail, droplet detected, and false droplet states. The state machine may identify double-peak waveforms and single-peak waveforms using different criteria.

Figure 26:
FIG. 26 is an exemplary double-peak waveform present in a deflection signal and marked from left to right with vertical bars at a leading end, a first local maximum, a local minimum, a second local maximum, and a trailing end of the waveform.

The state machine may begin in idle state 372 when the state machine is activated. State machine 370 may remain in the idle state until the deflection signal rises by more than a threshold value (the "head threshold") above baseline. The state machine then changes to head state 374. FIG. 26 shows a head or first rising section 386 corresponding to head state 374 for a waveform 246. Rising section 386 extends from a leading end of the waveform to a local maximum. The state machine may remain in the head state until a local maximum greater than a local maximum threshold is found, and then converts to dip-1 state 376, or changes to false droplet state 384 and returns to idle state 372 if the local maximum is less than the local maximum threshold.

State machine 370 remains in dip-1 state 376 as the deflection signal falls. FIG. 26 shows a first dip or falling section 388 corresponding to dip-1 state 376 for waveform 246. Falling section 388 extends from the first local maximum to a local minimum. The state machine may remain in the dip-1 state until a local minimum less than a local minimum threshold is found, and then changes to dip-2 state 378, or changes to false droplet state 384, and returns to idle state 372 if the local minimum is greater than the local minimum threshold.

State machine 370 remains in dip-2 state 378 as the deflection signal rises. FIG. 26 shows a second dip or rising section 390 corresponding to dip-2 state 378 for waveform 246. Rising section 390 extends from the local minimum to a second local maximum. The state machine may remain in the dip-2 state until a local maximum greater than a local maximum threshold is found, and then changes to tail state 380, or changes to false droplet state 384, and returns to idle state 372 if the local maximum is less than the local maximum threshold.

State machine 370 remains in tail state 380 as the deflection signal falls. FIG. 26 shows a second falling or tail section 392 corresponding to tail state 380 for waveform 246. Falling section 392 extends from the second local maximum to the trailing end of the waveform. The state machine may remain in the tail state until the deflection signal drops below a tail threshold, and then changes to droplet detected state 382 and returns to idle 372, or changes to false droplet state 384 and returns to idle state 372 if the deflection signal fails to drop below the tail threshold. Accordingly, the state machine may or may not be configured to exclude waveforms (and corresponding droplets) that overlap one another more than a threshold amount.

The state machine further may be configured to exclude waveforms (and corresponding droplets) based on any other suitable criteria, such as one or both local maxima being greater than a threshold, the local minimum being less than a threshold, and/or the like.

Figure 27:
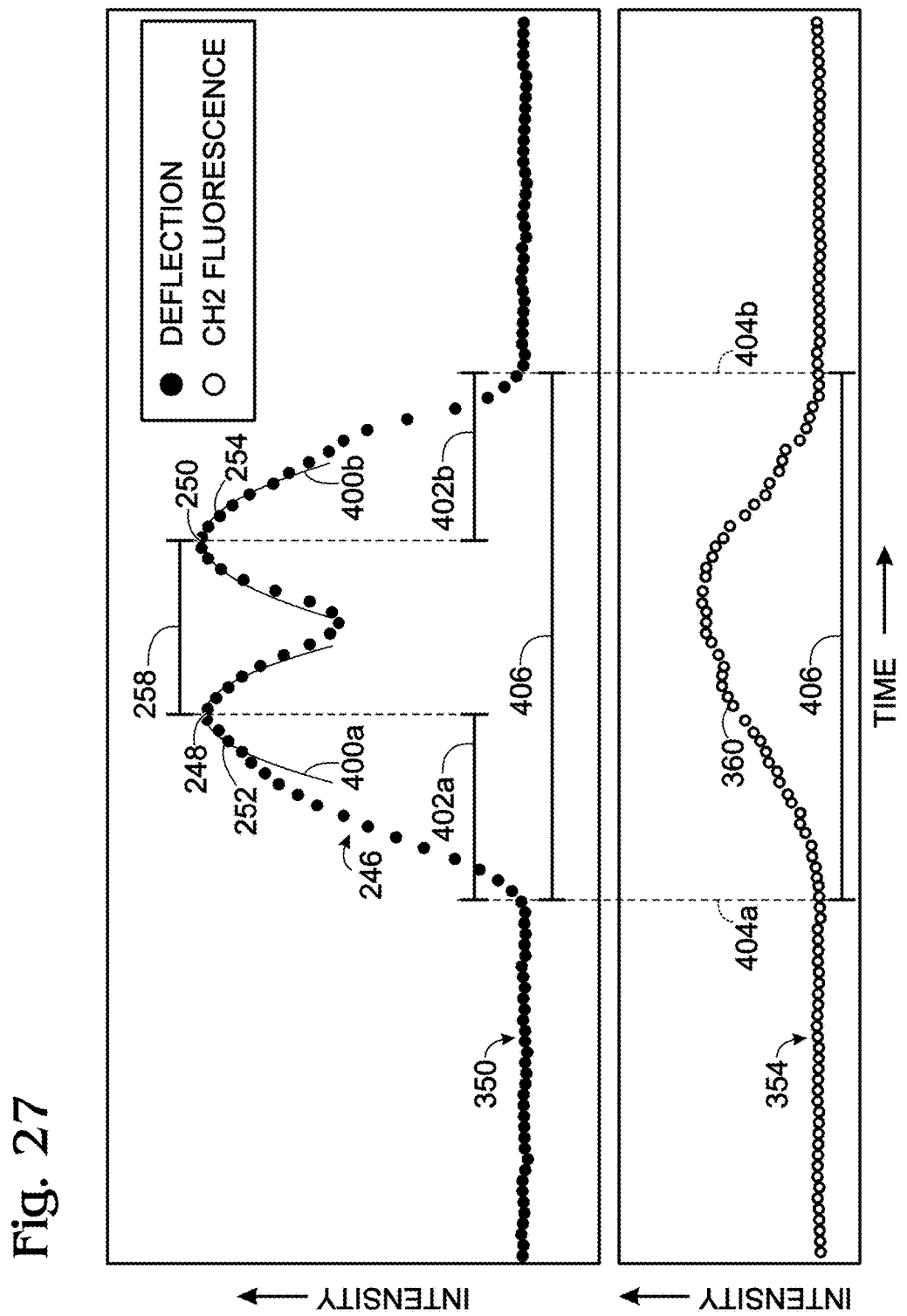
FIG. 27 is a pair of graphs created with the deflection signal and one of the fluorescence signals of FIG. 24, and schematically illustrating how a double-peak waveform produced by the deflection signal is analyzed by the algorithm of FIGS. 23A and 23B to obtain a peak-to-peak separation value for the waveform and integration boundaries for the fluorescence signal from time points of the peaks, in accordance with aspects of the present disclosure.

FIG. 27 shows a pair of graphs created with deflection signal 350 and photoluminescence signal 354 of FIG. 24. The graphs are marked to schematically illustrate how a waveform 246 produced by deflection signal 350 may be analyzed by algorithm 310 of FIGS. 23A and 23B to obtain a peak-to-peak separation value 258 for the waveform. Respective curves 400a, 400b may be fitted to points of each hump 252, 254. Each curve may, for example, be a second order polynomial. Peaks 248, 250 may be defined by the respective maximum value of each curve. The process of curve fitting provides a more accurate time value for each peak relative to selecting one of the data points of each hump as the local maximum, and therefore produces a more accurate separation value 258.

The temporal value of each peak 248, 250 may be adjusted by respective offsets 402a, 402b to define integration boundaries 404a, 404b for pulse 360 of photoluminescence signal 354. More particularly, offset 402a may be subtracted from the temporal value of peak 248, and offset 402b may be added to the temporal value of peak 250, to define the respective integration boundaries for pulse 360. Each offset may be a fixed value used for each waveform, and offsets 402a, 402b may be the same or different from one another. Each offset may or may not be predefined before the beginning of the run. The offset may represent an average offset determined from a set of waveforms. Photoluminescence signal 354 may be integrated over a span 406 extending between integration boundaries 404a, 404b to obtain an integrated amplitude (an integrated intensity).

Figure 28:
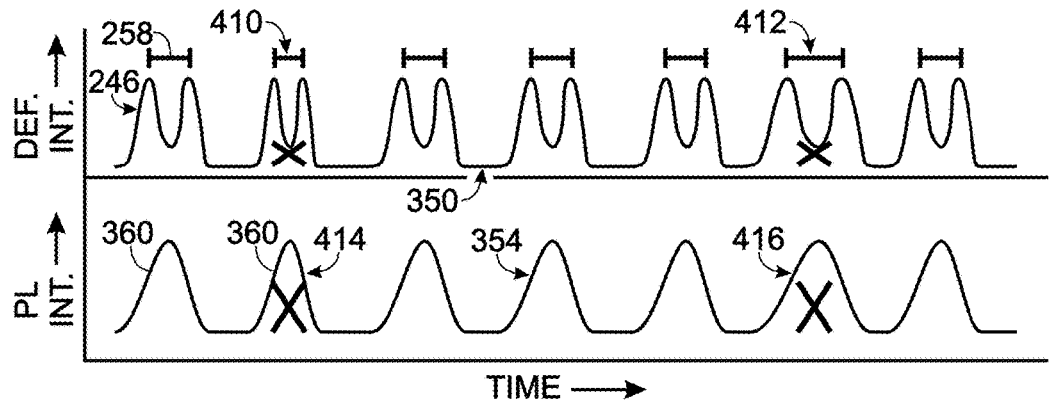
FIG. 28 is a pair of graphs schematically representing a droplet-filtering process that may be performed to exclude droplets that correspond to double-peak waveforms having peak-to-peak separation values outside an acceptable range, in accordance with aspects of the present disclosure.
Figure 29:
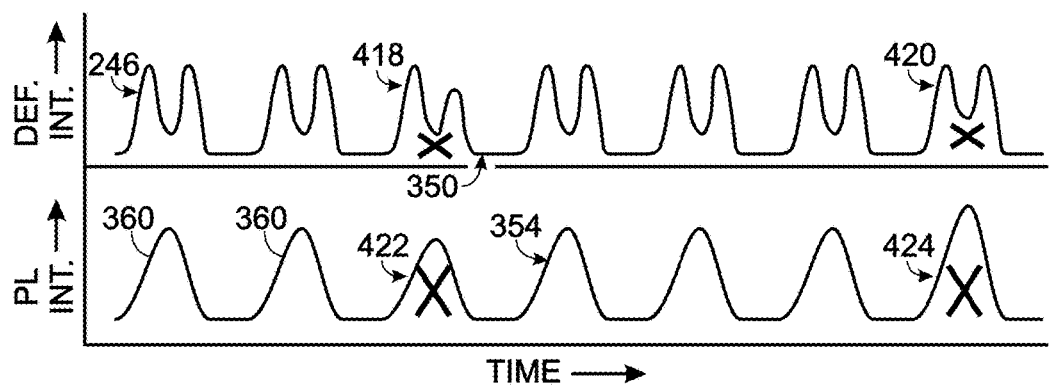
FIG. 29 is a pair of graphs schematically representing another droplet-filtering process that may be performed to exclude droplets corresponding to waveforms failing to meet one or more waveform criteria, in accordance with aspects of the present disclosure.
Figure 30:
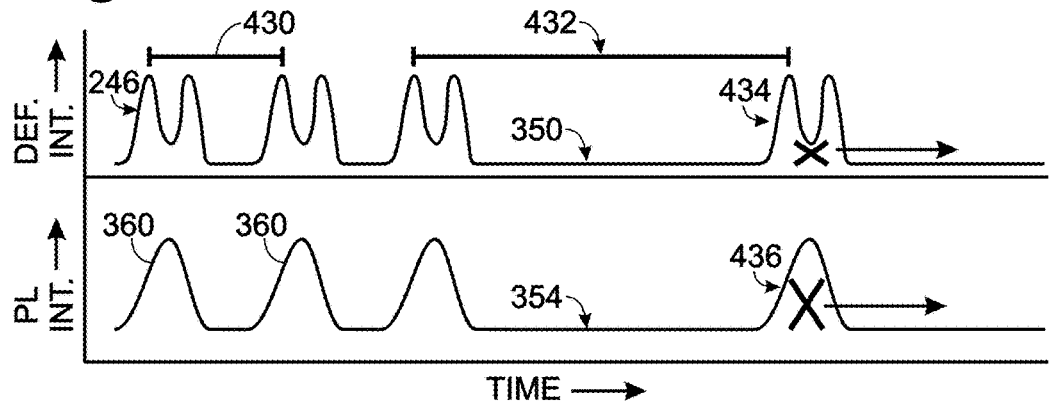
FIG. 30 is a pair of graphs schematically representing yet another droplet-filtering process that may be performed to exclude droplets (and the rest of each signal) detected after a sufficient change in the frequency and period of waveforms in the deflection signal, in accordance with aspects of the present disclosure.

FIGS. 28-30 show a series of graphs schematically depicting droplet-filtering processes that may be performed on waveforms of deflection signal 350 and amplitudes obtained from photoluminescence signal 354. Each deflection signal is plotted as deflection intensity (DEF. INT.) as a function of time. The photoluminescence signal is plotted as photoluminescence intensity (PL INT.) as a function of time. Each filtering process eliminates droplets and thus portions of the photoluminescence signal (and deflection signal) from further consideration, as indicated by an "X" under individual waveforms 246 of signal 350 and pulses 360 of signal 354. The filtering process filters droplets based on deflection signal 350.

FIG. 28 shows droplets (via signals 350 and 354) being filtered based on a width value, namely, a peak-to-peak separation value 258. The separation values indicated at 410 and 412 deviate by more than a threshold from an average of the separation values. Droplets, waveforms, and pulses 414, 416 temporally corresponding to the waveforms that produced separation values 410, 412 are excluded.

FIG. 29 shows droplets (via signals 350 and 354) being filtered based on one or more quality metrics of waveforms of deflection signal 350. Waveforms indicated at 418, 420 each have a quality metric that does not meet a threshold condition, which causes droplets associated with waveforms 418, 420 and pulses 422, 424 to be excluded. In the example of FIG. 29, waveform 418 has a ratio of the pair of local maxima that exceeds a threshold. Also, waveform 420 has a ratio of a local maximum to the local minimum that exceeds a threshold. In other embodiments, state machine 370 may be configured to perform any suitable quality filtering of waveforms, such that additional quality filtering is not needed. Identification of waveforms may be considered to be performed by state machine 370 alone or in combination with additional quality filtering.

FIG. 30 shows droplets (via signals 350 and 354) being filtered based on a period 430 between waveforms 246 of deflection signal 350. Period 430 is inversely related to a frequency of the waveforms. Exceeding a threshold change in the period or frequency may cause the rest of the deflection signal and/or photoluminescence signal detected after the change to be ignored. In FIG. 30, a significantly longer period 432 causes deflection waveform 434 of the deflection signal (and all subsequent deflection waveforms, if any) and photoluminescence pulse 436 (and all subsequent photoluminescence pulses) to be ignored.

FIG. 31 illustrates a less stringent approach, relative to that of FIG. 28, for identifying droplet waveforms and filtering the waveforms, to exclude a subset of the corresponding droplets from further consideration. The approach of FIG. 31 allows a broader size range of droplets to be used for calculating analyte content. In FIG. 28, each droplet produces a double-peak waveform in the deflection signal, and only a subset of the double-peak waveforms (and thus the corresponding droplets) are considered to have an acceptable width value measured from peak-to-peak within each waveform. However, the size of droplets may vary too much within an emulsion or among emulsions, to accept only droplets generating double-peak waveforms for calculating analyte content. Otherwise, too many droplets (and entire emulsions) may be rendered useless for analyte analysis.

FIG. 31 shows a pair of graphs schematically depicting a deflection signal 350 and a photoluminescence signal 354 detected over the same time period from droplets (or other particles) passing serially through an irradiation zone of a channel. Deflection signal 350 includes particle waveforms 440a to 440e generated by a series of droplets. Photoluminescence signal represents an analyte and has a series of signal pulses 442a to 442e also generated by the series of droplets and temporally corresponding to the waveforms.

Due to variation in droplet volume, waveforms 440a, 440c, and 440d are double-peak waveforms including a pair of local maxima of approximately the same amplitude. In contrast, waveforms 440b and 440e are single-peak waveforms having only one local maximum. The double-peak waveforms may be produced by larger droplets, and the single-peak waveforms by smaller droplets.

Both types of waveforms may be identified by a modified version of the state machine described above for FIG. 25. In particular, the state machine may look for double-peak waveforms and single-peak waveforms in the deflection signal, that meet respective sets of criteria. In some cases, the state machine may search each successive section of the deflection signal for a double-peak waveform and, if the search is not successful, then for a single-peak waveform.

A respective width value 444a to 444e may be calculated for each particle waveform 440a to 440e. The width values may be described as waveform widths and are illustrated schematically. Each width may be measured between a leading time point 446 and a trailing time point 448 of the corresponding waveform at the same amplitude. (Time points 446 and 448 are connected by a dashed line 450 in each waveform.) The amplitude at which each width is measured may, for example, be proportional to a characteristic amplitude of the waveform (optionally after subtraction of baseline from both amplitudes).

In the depicted embodiment, the respective amplitude for width measurement of each waveform is a constant fraction of the characteristic amplitude at a time point 452 at which the slope of a leading region 454 of the waveform reaches a maximum. Leading region 454 rises at least generally from baseline to a first (or only) local maximum of the waveform.

Width values 444a to 444e may be filtered to exclude droplets that are outside of an acceptable size range, as described above. Droplets having width values that deviate by more than a threshold from the average of the width values may be excluded and will not contribute to the final result of the assay. For example, waveform 440b has a width value that is below the accepted minimum width value, as indicated by an "X" under waveform 440b and under temporally corresponding photoluminescence pulse 442b. Accordingly, pulse 442b does not contribute to the number of droplets that are assigned as positive or as negative for the analyte, or to the total number of droplets. Exclusion of waveform 440b, pulse 442b, and/or the corresponding droplet from further consideration may be performed at any suitable time.

Amplitudes may be obtained from pulses 442a, 442c, 442d, and 442e, such as by integration of the photoluminescence signal. The boundaries for integration of each pulse may be the leading and trailing time points used for calculating the width value of the corresponding deflection waveform, optionally with a temporal offset to each time point, as described above. The amplitudes may be compared to at least one threshold to assign each droplet as positive or as negative for the analyte. The number of droplets that are positive or that are negative for the analyte may be enumerated, and the total number of droplets may be enumerated. Each number may not represent any droplets that failed to meet one or more criteria as described above. A concentration of the analyte may be calculated using the numbers and a volume of the droplets.

XI. EXAMPLES

The following examples describe selected aspects and embodiments of the present disclosure related to detection and signal processing for particle assays. These examples are included for illustration and are not intended to limit or define the entire scope of the present disclosure.

Example 1. Further Optical Aspects of Detection and Processing Systems

This example describes further exemplary optical aspects of detection and processing systems.

The detection and processing system may be based on focused light of any detectable wavelength being deflected by a particle, such as a droplet, while the particle is in the detection volume. For the case of optically transparent particles, at least three mechanisms (e.g., Mie scattering, refraction, and reflection) can come into play. The detection of deflected light may be accompanied with measuring the fluorescence intensity originating from dye molecules inside particles, such as droplets. The same light source may be used to generate deflection and fluorescence signals, and thus optical radiation from the light source may be referred to as excitation light. Processing of synchronously-acquired deflection and fluorescence signals increases the accuracy of the amplitude and span of the fluorescence signal of each particle, in particular for particles having only weak (or no) fluorescence.

The detection and processing system is based on blocking a fraction of the collimated excitation light before it is focused by an objective into a detection volume. An air slit and the magnification produced by a collimating lens and a focusing objective may define a detection volume inside a flow channel. A line mask may be located at the back focal plane of the focusing objective or, when the back focal plane is inaccessible, as close to it as possible. Most large-magnification objectives have the back focal plane inside their bodies. Testing was performed with a line mask constituted by a thin, straight black wire. The wire was mounted to the back aperture of the focusing objective. The direction of the wire was aligned with the direction of the air slit. The focusing objective creates an image of the line mask at a certain distance behind the detection volume. The closer the line mask to the objective's back focal plane, the greater the distance between the detection volume and the line mask image; the image is created at infinity when the line mask is exactly at the objective back focal plane. Therefore, outward of the back side of the flow channel (i.e., to the right of channel 60 in FIG. 1), there exists a shadow region created by the line mask. Another air slit may block light outside of the shadow region, and a light detector may detect light intensity right behind the air slit.

The air slit in front of the deflection detector may be selected to have its width slightly narrower than the line mask image and its direction may be aligned with the direction of the line mask image. Thus, the deflection detector stays in darkness until a particle enters the detection volume. The presence of the particle changes the paths of light rays across the detection volume and some light reaches the deflection detector, creating a deflection signal.

The disclosed detection scheme is different from the layout of a forward scattering channel used in many flow cytometers. In the case of forward scattering, a narrow laser beam, focused with a relatively long focal length lens (e.g., 50-100 mm) into a flow channel, is entirely blocked with an opaque optical stop at the other side of the channel, while small angle scattered light is detected around the stop.

The detection and processing system disclosed herein has various advantages over flow cytometers having a forward scattering channel. First, there may be no need to use a high quality laser beam, i.e., a beam that is both narrow and well-collimated. Instead, the detection and processing system disclosed herein was tested with low-cost, high-power LEDs coupled to multimode optical fibers, as well as with diode lasers coupled to the same multimode optical fibers, and demonstrated comparable performance with the different light sources. In fact, any light source that can be coupled into a large-core optical fiber and then collimated may be suitable for the detection of deflected light, as described herein. Second, there may be no need to use a second objective to collect fluorescence. In many flow cytometry instruments, a separate high numerical aperture objective mounted at 90 degrees with respect to the excitation laser optical path collects light emitted by fluorescence. The focusing objective of the present disclosure may be configured to have a short working distance and high numerical aperture, which allows construction of an epi-fluorescence confocal layout, as shown in FIG. 1, where the same objective focuses the irradiation/excitation beam on the detection volume and collects light emitted by fluorescence. The registered fluorescence amplitudes shown in FIG. 21 were acquired in an epi-fluorescence confocal mode.

A black line mask at the main objective back aperture creates a shadow across the illuminated area at the opposite side of a flow chip (a planar member defining a flow channel). The shadow half angle is two degrees. A photodiode with an air slit in front of it normally stays in the shadow. Once a droplet enters the detection volume, the droplet deflects some of the excitation light, which passes through the slit and generates photocurrent. With a droplet-diameter-to-wavelength ratio around 100, Mie theory predicts negligible scattering at angles above two degrees, so the detection mechanism may be based on droplet "lensing" due to a lower refractive index of water (1.33) than silicone oil (1.39). The mask preferentially may be a long line due to a round flow channel serving as a negative power cylindrical lens, such that a round spot mask (a point mask) creates little shadow. The mask does not interfere with the image formation of a telescope's slit, i.e., the detection area is still a sharp, uniformly-illuminated line. Total light losses due to both excitation light and fluorescence being masked by the mask may stay below 5, 4, 3, or 2 percent, among others.

Example 2. Further Aspects of Signal Processing

This example describes further exemplary aspects of signal processing. The present disclosure provides methods and apparatus for analyzing data detected from particles, such as droplets. In some embodiments, the methods and apparatus include and/or utilize an algorithm for identifying droplet position and characterizing peaks of droplets from a deflection signal.

The present disclosure provides methods of automatically determining droplet position, size, and fluorescence signal values in one or multiple fluorescence channels using data collected from droplets. An exemplary method comprises a) providing an algorithm to determine the temporal positions of droplets from a deflection signal, b) calculating a size characteristic of each droplet from the deflection signal, c) calculating a signal value for one or multiple fluorescence channels for each droplet detected with the deflection signal, and d) providing droplet characterization information for further analysis including filtering/gating droplets by applying gating, thresholding/clustering to the signal values.

An algorithm utilizing a deflection signal may comprise the following steps. First, peaks of droplets may be detected by identifying signatures of a droplet waveform in a deflection signal. Multiple signatures, e.g., double peaks of single droplets, leading and trailing edges, etc. can be utilized to identify droplets. A droplet position is calculated once the droplet signature is found. Second, a droplet size characteristic may be calculated based on the distance between two peaks of the droplet in the deflection signal, or the temporal distance between the leading and trailing edges (ends) of the droplet's waveform. Third, droplet amplitudes in each fluorescence channel may be determined by integrating each fluorescence signal with subtraction of the baseline. Fourth, the algorithm may repeat the preceding three steps until it finishes analyzing all of the waveforms in the data. Fifth, the algorithm may apply a color calibration to the droplet amplitudes for different fluorescence channels to decouple crosstalk among them. Width correction, gating and clustering may be applied afterwards for further data analysis.

Example 3. Selected Embodiments A

This example describes selected embodiments of the present disclosure as a series of indexed paragraphs. These embodiments should not limit the entire scope of the present disclosure.

Paragraph 1. A system for detecting and processing signals from particles, comprising: (A) two or more detectors configured to detect at least one photoluminescence signal and a deflection signal from particles passing through a detection volume; and (B) a processor configured to (i) identify waveforms in the deflection signal, at least a subset of the waveforms having a particle signature that includes a pair of peaks corresponding to a particle entering and exiting the detection volume, (ii) obtain an amplitude temporally corresponding to each of a plurality of the waveforms from each photoluminescence signal, and (iii) determine a number of particles having a given analyte content based on at least a subset of the amplitudes.

Paragraph 2. The system of paragraph 1, wherein the processor is configured to obtain a characterizing value for individual waveforms, and to exclude particles from the number determined based on the characterizing values.

Paragraph 3. The system of paragraph 2, wherein the characterizing value of the at least a subset of waveforms having the particle signature individual waveform is a separation value representing a time interval between the pair of peaks of the individual waveform.

Paragraph 4. The system of paragraph 2 or 3, wherein the processor is configured to adjust the characterizing values obtained from the individual waveforms to correct for fluctuations in flow rate through the detection volume as the signals are being detected, and to exclude particles based on adjusted characterizing values.

Paragraph 5. The system of paragraph 4, wherein the processor is configured to adjust the characterizing values with a spline.

Paragraph 6. The system of paragraph 2, wherein the characterizing value of each individual waveform is a ratio of at least one peak and a local minimum between the pair of peaks of the individual waveform.

Paragraph 7. The system of any of paragraphs 2 to 6, wherein the processor is configured to compare each characterizing value to a threshold, and to exclude a particle corresponding to the characterizing value if the characterizing value exceeds the threshold.

Paragraph 8. The system of any of paragraphs 2 to 7, wherein the processor is configured to calculate a mean of the characterizing values, and to exclude particles corresponding to characterizing values that deviate by more than a threshold from the mean.

Paragraph 9. The system of paragraph 8, wherein the processor is configured to calculate the threshold based on a distribution of the characterizing values with respect to the mean.

Paragraph 10. The system of paragraph 9, wherein the processor is configured to calculate a standard deviation for the characterizing values, and to calculate the threshold based on the standard deviation.

Paragraph 11. The system of any of paragraphs 1 to 10, wherein the processor is configured to identify waveforms in real time with a state machine.

Paragraph 12. The system of any of paragraphs 1 to 11, wherein the processor is configured to obtain each amplitude by integrating a portion of a photoluminescence signal based on integration boundaries defined with one of the plurality of waveforms, optionally using a temporal position of at least one peak of the one waveform to define at least one of the boundaries.

Paragraph 13. A system for detecting and processing signals from particles, comprising: (A) two or more detectors configured to detect at least one photoluminescence signal and a deflection signal from particles passing through a detection volume; and (B) a processor configured to (i) identify waveforms in the deflection signal, each waveform having a particle signature that includes a pair of peaks corresponding to a particle entering and exiting the detection volume, (ii) obtain a peak-to-peak separation value for individual waveforms, (iii) exclude particles, at least in part based on the separation values, (iv) obtain an amplitude temporally corresponding to each of a plurality of the waveforms from each photoluminescence signal, and (v) determine a number of non-excluded particles having a given analyte content based on at least a subset of the amplitudes.

Paragraph 14. The system of paragraph 13, wherein the processor is configured to determine a number of particles that are positive or that are negative for an analyte using amplitudes representing only non-excluded particles.

Paragraph 15. The system of paragraph 13 or 14, wherein the processor is configured to identify waveforms with a state machine.

Paragraph 16. The system of paragraph 15, wherein the state machine includes four states representing a first rising section, a first falling section, a second rising section, and a second falling section of a waveform.

Paragraph 17. The system of any of paragraphs 13 to 16, wherein the processor is configured to identify waveforms in real time as the signals are being detected.

Paragraph 18. The system of any of paragraphs 13 to 17, wherein the processor is configured to stop passing particles from a same set of emulsion through the detection volume when a frequency of waveforms or a period between waveforms in the deflection signal meets a condition.

Paragraph 19. The system of any of paragraphs 13 to 18, wherein the processor is configured to fit a pair of curves to each of the individual waveforms, define a pair of points of the curves representing the pair of peaks of the individual waveform, and calculate the separation value for the individual waveform as a time difference between the pair of points.

Paragraph 20. The system of paragraph 19, wherein each curve is defined by a second order polynomial.

Paragraph 21. The system of any of paragraphs 13 to 20, wherein the processor is configured to integrate portions of each photoluminescence signal to obtain the amplitudes, and wherein each amplitude optionally represents an integrated intensity with background subtracted.

Paragraph 22. The system of any of paragraphs 13 to 21, wherein the processor is configured to define a leading boundary and a trailing boundary for each of the plurality of waveforms, and to integrate each photoluminescence signal over an interval defined between the leading and trailing boundaries to obtain an amplitude corresponding to the waveform from the photoluminescence signal, and wherein, optionally, each boundary is defined at a fixed distance along a time axis from a peak of the waveform.

Paragraph 23. The system of any of paragraphs 13 to 22, wherein the processor is configured to adjust the separation values calculated from the individual waveforms to correct for fluctuations in flow rate through the detection volume that occur as the signals are being detected, and wherein the processor is configured to exclude particles based on the separation values after the separation values have been adjusted.

Paragraph 24. The system of paragraph 23, wherein the processor is configured to adjust the separation values with a spline.

Paragraph 25. The system of any of paragraphs 13 to 24, wherein the processor is configured to calculate a mean of the separation values, and to exclude each particle temporally corresponding to a separation value that deviates by more than a threshold from the mean of the separation values.

Paragraph 26. The system of paragraph 25, wherein the processor is configured to calculate the threshold based on a distribution of the separation values with respect to the mean of the separation values.

Paragraph 27. The system of paragraph 26, wherein the processor is configured to calculate a standard deviation of the separation values, and to calculate the threshold based on the standard deviation.

Paragraph 28. The system of paragraph 27, wherein the threshold is calculated by multiplying the standard deviation by a value.

Paragraph 29. The system of any of paragraphs 13 to 28, wherein the processor is configured also to exclude particles based on one or more waveform criteria other than the separation values, before the number is determined.

Paragraph 30. The system of any of paragraphs 13 to 29, wherein the processor is configured to determine the number at least in part by assigning individual particles as positive or negative for an analyte using at least a subset of the amplitudes.

Paragraph 31. The system of paragraph 30, wherein the processor is configured to compare each of a plurality of the amplitudes to at least one threshold and to assign individual particles as positive or negative for an analyte based on comparing each of the plurality of amplitudes.

Paragraph 32. The system of any of paragraphs 13 to 31, wherein the processor is configured to calculate a concentration of an analyte using the number determined.

Paragraph 33. A method of detecting and processing signals from particles, the method comprising: (A) detecting at least one photoluminescence signal and a deflection signal from particles passing through a detection volume; (B) identifying waveforms in the deflection signal, each waveform having a particle signature that includes a pair of peaks corresponding to a particle entering and exiting the detection volume; (C) obtaining an amplitude temporally corresponding to each of a plurality of the waveforms from each photoluminescence signal; and (D) determining a number of particles having a given analyte content based on at least a subset of the amplitudes.

Paragraph 34. The method of paragraph 33, further comprising a step of obtaining a characterizing value for individual waveforms, and a step of excluding particles from the number determined based on the characterizing values.

Paragraph 35. The method of paragraph 34, wherein the characterizing value of each waveform is a separation value representing a time interval between the pair of peaks of the waveform.

Paragraph 36. The method of paragraph 34 or 35, further comprising a step of adjusting the characterizing values calculated from the waveforms to correct for fluctuations in flow rate through the detection volume as the signals are being detected, wherein the step of excluding particles uses adjusted characterizing values.

Paragraph 37. The method of paragraph 36, wherein the step of adjusting the characterizing values includes a step of adjusting the characterizing values with a spline.

Paragraph 38. The method of paragraph 34, wherein the characterizing value of each individual waveform is a ratio involving at least one peak and a local minimum between the pair of peaks of the individual waveform.

Paragraph 39. The method of any of paragraphs 34 to 38, wherein the step of excluding particles includes a step of comparing each characterizing value to a threshold, and a step of excluding a particle corresponding to the characterizing value if the characterizing value exceeds the threshold.

Paragraph 40. The method of any of paragraphs 34 to 39, further comprising a step of calculating a mean of the characterizing values, wherein the step of excluding particles includes a step of excluding particles temporally corresponding to characterizing values that deviate by more than a threshold from the mean.

Paragraph 41. The method of paragraph 40, further comprising a step of calculating the threshold based on a distribution of the characterizing values with respect to the mean.

Paragraph 42. The method of paragraph 41, further comprising a step of calculating a standard deviation of the characterizing values, and a step of calculating the threshold based on the standard deviation.

Paragraph 43. The method of any of paragraphs 33 to 42, wherein the step of identifying waveforms is performed in real time with a state machine.

Paragraph 44. The method of any of paragraphs 33 to 43, wherein the step of obtaining an amplitude includes a step of integrating a portion of a photoluminescence signal based on integration boundaries defined with one of the plurality of waveforms, optionally using a temporal position of at least one peak of the one waveform to define at least one of the boundaries.

Paragraph 45. The method of any of paragraphs 33 to 44, further comprising a step of stopping passage of particles from a same emulsion through the detection volume when a frequency of waveforms or a period between waveforms meets a condition.

Paragraph 46. A method of detecting and processing signals from particles, the method comprising: (A) detecting at least one photoluminescence signal and a deflection signal from particles passing through a detection volume; (B) identifying waveforms in the deflection signal, each waveform having a particle signature that includes a pair of peaks corresponding to a particle entering and exiting the detection volume; (C) calculating a peak-to-peak separation value for individual waveforms; (D) excluding particles, at least in part based on the separation values; (E) obtaining an amplitude temporally corresponding to each of a plurality of the waveforms from each photoluminescence signal, and (F) determining a number of non-excluded particles having a given analyte content based on at least a subset of the amplitudes.

Paragraph 47. The method of paragraph 46, wherein the step of determining a number includes a step of determining a number of particles that are positive or that are negative for an analyte using amplitudes representing only non-excluded particles.

Paragraph 48. The method of paragraph 46 or 47, wherein the step of identifying waveforms is performed with a state machine.

Paragraph 49. The method of any of paragraphs 46 to 48, wherein the step of identifying waveforms is performed in real time as the signals are being detected.

Paragraph 50. The method of any of paragraphs 46 to 49, further comprising a step of stopping passage of particles through the detection volume when a frequency of waveforms or a period between waveforms meets a condition.

Paragraph 51. The method of any of paragraphs 46 to 50, further comprising a step of fitting a pair of curves to each of the individual waveforms, and a step of defining a pair of points of the curves representing the pair of peaks, wherein the step of calculating a peak-to-peak separation value includes a step of calculating a time difference between the pair of points.

Paragraph 52. The method of any of paragraphs 46 to 51, wherein the step of obtaining an amplitude includes a step of integrating portions of each photoluminescence signal to obtain the amplitudes, and wherein each amplitude optionally represents an integrated intensity with background subtracted.

Paragraph 53. The method of any of paragraphs 46 to 52, further comprising a step of defining a leading boundary and a trailing boundary for each of the plurality of waveforms, wherein the step of obtaining an amplitude includes a step of integrating each photoluminescence signal over an interval defined between the leading and trailing boundaries, and wherein, optionally, each boundary is defined at a fixed distance along a time axis from a peak of the waveform.

Paragraph 54. The method of any of paragraphs 46 to 53, further comprising a step of adjusting the separation values calculated from the individual waveforms to correct for fluctuations in flow rate through the detection volume that occur as the signals are being detected, wherein the step of excluding particles uses separation values after the separation values have been adjusted.

Paragraph 55. The method of paragraph 54, wherein the step of adjusting the separation values includes a step of adjusting the separation values with a spline.

Paragraph 56. The method of any of paragraphs 46 to 55, further comprising a step of calculating a mean of the separation values, wherein the step of excluding particles includes a step of excluding particles temporally corresponding to separation values that deviate by more than a threshold from the mean of the separation values.

Paragraph 57. The method of paragraph 56, further comprising a step of calculating the threshold based on a distribution of the separation values.

Paragraph 58. The method of paragraph 57, further comprising a step of calculating a standard deviation from the separation values, and a step of calculating the threshold based on the standard deviation.

Paragraph 59. The method of paragraph 58, wherein the step of calculating the threshold includes a step of multiplying the standard deviation by a constant.

Paragraph 60. The method of any of paragraphs 46 to 59, wherein the step of excluding particles includes a step of excluding particles based on one or more waveform criteria other than the separation values.

Paragraph 61. The method of any of paragraphs 46 to 60, wherein the step of determining a number includes a step of assigning individual particles as positive or negative for an analyte.

Paragraph 62. The method of paragraph 61, wherein the step of assigning includes a step of comparing each of a plurality of amplitudes to at least one threshold, and a step of assigning individual particles as positive or negative based on the step of comparing.

Paragraph 63. The method of any of paragraphs 46 to 62, further comprising a step of calculating a concentration of an analyte using the number determined.

Paragraph 64. The method of any of paragraphs 46 to 63, further comprising a step of stopping passage of particles from a same emulsion through the detection volume when a frequency of waveforms or a period between waveforms meets a condition.

Example 4. Selected Embodiments B

This example describes further selected embodiments of the present disclosure as a series of indexed paragraphs. These embodiments should not limit the entire scope of the present disclosure.

Paragraph 1. A method of detecting and processing signals from particles, the method comprising: (A) passing particles through a zone of a channel, wherein each particle includes a label, and only a subset of the particles include an analyte; (B) irradiating the zone with light generated by at least one light source, wherein interaction of the light with the particles deflects a portion of the light and induces photoluminescence from the label; (C) detecting a deflection signal and a photoluminescence signal from the zone with a pair of detectors; (D) identifying particle waveforms in the deflection signal, the particle waveforms corresponding to respective particles, at least a subset of the particle waveforms being double-peak waveforms including a pair of peaks corresponding to a particle entering and exiting the zone; (E) obtaining amplitudes from the photoluminescence signal, the amplitudes corresponding to respective particles and their particle waveforms, at least a subset of the amplitudes corresponding to the double-peak waveforms; and (F) assigning individual particles as positive or as negative for the analyte based on the corresponding amplitudes.

Paragraph 2. The method of paragraph 1, further comprising a step of determining a number of particles assigned as positive or assigned as negative for the analyte.

Paragraph 3. The method of paragraph 1 or paragraph 2, further comprising a step of calculating respective width values for the particle waveforms, and a step of excluding a subset of the particles based on the respective width values.

Paragraph 4. The method of paragraph 3, further comprising a step of determining a number of the particles assigned as positive or assigned as negative for the analyte, and a step of calculating a concentration of the analyte using the number and a total number of the particles, and wherein the subset of the particles that are excluded contributes neither to the number assigned as positive or assigned as negative for the analyte nor to the total number.

Paragraph 5. The method of paragraph 3 or paragraph 4, further comprising a step of adjusting the width values calculated from the particle waveforms to obtain adjusted width values that correct for fluctuations in flow rate through the zone as the signals are being detected, wherein the step of excluding is based on the adjusted width values, and wherein the fluctuations in flow rate are determined from the deflection signal.

Paragraph 6. The method of any of paragraphs 3 to 5, further comprising a step of determining a respective amplitude of the deflection signal at which to calculate the width value for each waveform based on a characteristic of the waveform.

Paragraph 7. The method of paragraph 6, wherein the respective amplitude of the deflection signal is a first amplitude, wherein the characteristic of the waveform is a second amplitude of the deflection signal at which a slope of the deflection signal is at a maximum within at least a region of the waveform, further comprising a step of calculating the first amplitude using the second amplitude.

Paragraph 8. The method of any of paragraphs 3 to 7, further comprising a step of comparing each width value to at least one threshold, and a step of excluding a particle corresponding to the width value if the step of comparing meets a predefined condition.

Paragraph 9. The method of paragraph 8, further comprising a step of calculating an average of the width values, wherein the step of excluding a subset of the particles includes a step of excluding particles corresponding to width values that deviate by more than a defined amount from the average.

Paragraph 10. The method of paragraph 9, further comprising a step of calculating the defined amount based on a distribution of the width values with respect to the average.

Paragraph 11. The method of paragraph 9 or paragraph 10, further comprising a step of calculating a standard deviation for the width values, and a step of calculating the defined amount based on the standard deviation.

Paragraph 12. The method of any of paragraphs 1 to 11, wherein the step of identifying particle waveforms includes a step of identifying double-peak waveforms of the particle waveforms in real time.

Paragraph 13. The method of any of paragraphs 1 to 12, wherein the step of identifying particle waveforms includes a step of identifying double-peak waveforms with a state machine including four states representing a first rising section, a first falling section, a second rising section, and a second falling section of a double-peak waveform.

Paragraph 14. The method of any of paragraphs 1 to 13, wherein the step of identifying particle waveforms includes a step of identifying double-peak waveforms and single-peak waveforms.

Paragraph 15. The method of paragraph 14, wherein the step of identifying double-peak waveforms and single-peak waveforms includes a step of identifying double-peak waveforms using double-peak criteria and a step of identifying single-peak waveforms using at least one single-peak criterion that is different from any of the double-peak criteria.

Paragraph 16. The method of any of paragraphs 1 to 15, wherein the step of obtaining amplitudes includes a step of calculating each amplitude by integrating a portion of the photoluminescence signal between integration boundaries defined with a corresponding particle waveform.

Paragraph 17. The method of paragraph 16, further comprising a step of calculating respective width values for the particle waveforms, and a step of establishing the integration boundaries for the portion of the photoluminescence signal using a pair of time points from which the width value for the corresponding particle waveform is calculated.

Paragraph 18. The method of paragraph 17, wherein the step of establishing the integration boundaries includes a step applying a temporal offset to each time point of the pair of time points.

Paragraph 19. The method of any of paragraphs 1 to 18, further comprising a step of stopping passage of particles from a same set of particles through the zone when a frequency of particle waveforms or a period between particle waveforms in the deflection signal meets a condition.

Paragraph 20. The method of any of paragraphs 1 to 19, wherein the zone has a width measured parallel to a direction of particle travel through the zone, wherein the particles have a dimension measured parallel to the direction of particle travel as each particle passes through the zone, and wherein the width of the zone is less than the dimension of the particles.

Paragraph 21. A system for detecting and processing signals from particles, comprising: (A) a channel; (B) one or more light sources configured to irradiate a zone within the channel; (C) at least one source of positive/negative pressure configured to drive particles in a carrier fluid through the zone; (D) a deflection detector configured to detect a deflection signal from particles passing through the zone; (E) a photoluminescence detector configured to detect a photoluminescence signal from particles passing through the zone; and (F) a processor configured to (i) identify particle waveforms in the deflection signal, at least a subset of the particle waveforms being double-peak waveforms including a pair of peaks corresponding to a particle entering and exiting the zone, (ii) obtain amplitudes from the photoluminescence signal, the amplitudes corresponding to respective particles and their particle waveforms, at least a subset of the amplitudes corresponding to the double-peak waveforms, and (iii) assign individual particles as positive or as negative for an analyte based on the corresponding amplitudes.

Paragraph 22. The system of paragraph 21, wherein the processor is configured to calculate respective width values for the particle waveforms, and to exclude a subset of the particles based on the respective width values.

Paragraph 23. The system of paragraph 22, wherein the processor is configured to define a leading boundary and a trailing boundary for each particle waveform, and to integrate the photoluminescence signal over an interval defined between the leading and trailing boundaries of the waveform to obtain one of the amplitudes, and wherein each boundary is defined at a fixed distance along a time axis from one of a pair of time points with which each corresponding width value is calculated.

Paragraph 24. The system of paragraph 22 or paragraph 23, wherein the processor is configured to determine a number of the particles that are assigned as positive or that are assigned as negative for the analyte, and to calculate a concentration of the analyte using the number and a total number of the particles, and wherein the subset of the particles that are excluded contributes neither to the number that are positive or that are negative for the analyte nor to the total number.

Paragraph 25. The system of any of paragraphs 22 to 24, wherein the processor is configured to adjust the width values calculated from the particle waveforms to obtain adjusted width values that correct for fluctuations in flow rate through the zone as the signals are being detected, and to exclude the subset of the particles based on the adjusted width values, and wherein the fluctuations in flow rate are determined from the deflection signal.

Paragraph 26. The system of paragraph 25, wherein the processor is configured to adjust the width values with a spline.

Paragraph 27. The system of any of paragraphs 22 to 26, wherein the processor is configured to determine an amplitude of the deflection signal at which to calculate the width value for each waveform based on a characteristic of the waveform.

Paragraph 28. The system of paragraph 27, wherein the amplitude is a first amplitude, wherein the characteristic of the waveform is a second amplitude of the deflection signal at which a slope of the deflection signal is at a maximum along a region of the waveform, and wherein the processor is configured to calculate the first amplitude using the second amplitude.

Paragraph 29. The system of any of paragraphs 22 to 28, wherein the processor is configured to compare each width value to at least one threshold, and to exclude a particle corresponding to the width value if comparing the width value to the at least one threshold meets a predefined condition.

Paragraph 30. The system of paragraph 29, wherein the processor is configured to calculate an average of the width values, and to exclude particles corresponding to width values that deviate by more than a defined amount from the average.

Paragraph 31. The system of paragraph 30, wherein the processor is configured to calculate the defined amount based on a distribution of the width values with respect to the average.

Paragraph 32. The system of any of paragraphs 21 to 31, wherein the processor is configured to identify the double-peak waveforms of the particle waveforms in real time.

Paragraph 33. The system of any of paragraphs 21 to 32, wherein the processor is configured to identify the double-peak waveforms of the particle waveforms with a state machine including four states representing a first rising section, a first falling section, a second rising section, and a second falling section of a double-peak waveform.

Paragraph 34. The system of any of paragraphs 21 to 33, wherein the processor is configured to identify double-peak waveforms and single-peak waveforms that are particle waveforms.

Paragraph 35. The system of paragraph 34, wherein the processor is configured to use at least one different criterion for identifying double-peak waveforms relative to single-peak waveforms.

Paragraph 36. The system of any of paragraphs 21 to 35, wherein the processor is configured to obtain each amplitude by integrating a portion of the photoluminescence signal between integration boundaries defined with a corresponding particle waveform.

Paragraph 37. The system of paragraph 36, wherein the processor is configured to calculate respective width values for the particle waveforms, and wherein the processor is configured to establish the integration boundaries for the portion of the photoluminescence signal using a pair of time points from which the width value for the corresponding particle waveform is calculated.

Paragraph 38. The system of paragraph 37, wherein the processor is configured to establish the integration boundaries by applying a temporal offset to each time point of the pair of time points.

Paragraph 39. The system of any of paragraphs 21 to 38, wherein the processor is configured to stop passing particles from a same set of particles through the zone when a frequency of particle waveforms or a period between particle waveforms in the deflection signal meets a condition.

The term "about," as used herein to describe a stated value, means within 10% of the stated value. For example, a dimension described as being "about 10" means that the dimension is greater than 9 and less than 11.

The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of detecting and processing signals from particles, the method comprising:
   passing particles through a zone of a channel, wherein each particle includes a label, and only a subset of the particles include an analyte;
   irradiating the zone with light generated by at least one light source, wherein interaction of the light with the particles deflects a portion of the light and induces photoluminescence from the label;
   detecting a deflection signal and a photoluminescence signal from the zone with a pair of detectors;
   identifying particle waveforms in the deflection signal with a processor, the particle waveforms corresponding to respective particles, at least a subset of the particle waveforms being double-peak waveforms including a pair of peaks corresponding to a particle entering and exiting the zone;
   obtaining amplitudes from the photoluminescence signal with the processor, the amplitudes corresponding to respective particles and their particle waveforms, at least a subset of the amplitudes corresponding to the double-peak waveforms; and
   assigning individual particles as positive or as negative for the analyte with the processor based on the corresponding amplitudes.

2. The method of claim 1, further comprising a step of determining a number of particles assigned as positive or assigned as negative for the analyte.

3. The method of claim 1, further comprising a step of calculating respective width values for the particle waveforms, and a step of excluding a subset of the particles based on the respective width values.

4. The method of claim 3, further comprising a step of determining a number of the particles assigned as positive or assigned as negative for the analyte, and a step of calculating a concentration of the analyte using the number and a total number of the particles, and wherein the subset of the particles that are excluded contributes neither to the number assigned as positive or assigned as negative for the analyte nor to the total number.

5. The method of claim 3, further comprising a step of adjusting the width values calculated from the particle waveforms to obtain adjusted width values that correct for fluctuations in flow rate through the zone as the signals are being detected, wherein the step of excluding is based on the adjusted width values, and wherein the fluctuations in flow rate are determined from the deflection signal.

6. The method of claim 3, further comprising a step of determining a respective amplitude of the deflection signal at which to calculate the width value for each waveform based on a characteristic of the waveform.

7. The method of claim 6, wherein the respective amplitude of the deflection signal is a first amplitude, wherein the characteristic of the waveform is a second amplitude of the deflection signal at which a slope of the deflection signal is at a maximum within at least a region of the waveform, further comprising a step of calculating the first amplitude using the second amplitude.

8. The method of claim 3, further comprising a step of comparing each width value to at least one threshold, and a step of excluding a particle corresponding to the width value if the step of comparing meets a predefined condition.

9. The method of claim 8, further comprising a step of calculating an average of the width values, wherein the step of excluding a subset of the particles includes a step of excluding particles corresponding to width values that deviate by more than a defined amount from the average.

10. The method of claim 9, further comprising a step of calculating the defined amount based on a distribution of the width values with respect to the average.

11. The method of claim 9, further comprising a step of calculating a standard deviation for the width values, and a step of calculating the defined amount based on the standard deviation.

12. The method of claim 1, wherein the step of identifying particle waveforms includes a step of identifying double-peak waveforms of the particle waveforms in real time.

13. The method of claim 1, wherein the step of identifying particle waveforms includes a step of identifying double-peak waveforms with a state machine including four states representing a first rising section, a first falling section, a second rising section, and a second falling section of a double-peak waveform.

14. The method of claim 1, wherein the step of identifying particle waveforms includes a step of identifying double-peak waveforms and single-peak waveforms.

15. The method of claim 14, wherein the step of identifying double-peak waveforms and single-peak waveforms includes a step of identifying double-peak waveforms using double-peak criteria and a step of identifying single-peak waveforms using at least one single-peak criterion that is different from any of the double-peak criteria.

16. The method of claim 1, wherein the step of obtaining amplitudes includes a step of calculating each amplitude by integrating a portion of the photoluminescence signal between integration boundaries defined with a corresponding particle waveform.

17. The method of claim 16, further comprising a step of calculating respective width values for the particle waveforms, and a step of establishing the integration boundaries for the portion of the photoluminescence signal using a pair of time points from which the width value for the corresponding particle waveform is calculated.

18. The method of claim 17, wherein the step of establishing the integration boundaries includes a step applying a temporal offset to each time point of the pair of time points.

19. The method of claim 1, further comprising a step of stopping passage of particles from a same set of particles through the zone when a frequency of particle waveforms or a period between particle waveforms in the deflection signal meets a condition.

20. The method of claim 1, wherein the zone has a width measured parallel to a direction of particle travel through the zone, wherein the particles have a dimension measured parallel to the direction of particle travel as each particle passes through the zone, and wherein the width of the zone is less than the dimension of the particles.

21. A system for detecting and processing signals from particles, comprising:
   a channel;
   one or more light sources configured to irradiate a zone within the channel;
   at least one source of positive/negative pressure configured to drive particles in a carrier fluid through the zone;
   a deflection detector configured to detect a deflection signal from particles passing through the zone;
   a photoluminescence detector configured to detect a photoluminescence signal from particles passing through the zone; and
   a processor configured to
      (i) identify particle waveforms in the deflection signal, at least a subset of the particle waveforms being double-peak waveforms including a pair of peaks corresponding to a particle entering and exiting the zone,
      (ii) obtain amplitudes from the photoluminescence signal, the amplitudes corresponding to respective particles and their particle waveforms, at least a subset of the amplitudes corresponding to the double-peak waveforms, and
      (iii) assign individual particles as positive or as negative for an analyte based on the corresponding amplitudes.

* * * * *